United States Patent [19]

Davis et al.

[11] Patent Number: 5,804,427
[45] Date of Patent: Sep. 8, 1998

[54] CYTOKINE-, STRESS-, AND ONCOPROTEIN-ACTIVATED HUMAN PROTEIN KINASE KINASES

[75] Inventors: Roger Davis, Princeton, Mass.; Joel Raingeaud, Bazoges en Pareds; Benoit Derijard, Marseilles, both of France

[73] Assignee: University of Massachusetts, Boston, Mass.

[21] Appl. No.: 446,083

[22] Filed: May 19, 1995

[51] Int. Cl.$^6$ .............................. C12N 9/12; C12N 9/00; C07K 1/00
[52] U.S. Cl. ........................ 435/194; 435/183; 530/350
[58] Field of Search .................... 435/183, 212, 435/226, 194; 530/350, 839

[56] References Cited

FOREIGN PATENT DOCUMENTS

WO 95/28421  10/1995  WIPO .

OTHER PUBLICATIONS

Davis, *Elsevier Science Ltd.,* TIBS 19:470–473, (1994).
Dérijard et al., *Science,* 267:682–685, (1995).
Freshney et al., *Cell,* 78:1039–1049, (1994).
Galcheva–Gargova et al., *Science,* 265:806–808, (1994).
Gupta et al., *Science,* 267:389–393, (1995).
Lin et al., *Science,* 268:286–290, (1995).
Minden et al., *Science,* 266:1719–1723, (1994).
Raingeaud et al., *The Journal of Biological Chemistry,* 270:7420–7426, (1995).
Rouse et al., *Cell,* 78:1027–1037, (1994).
Sanchez et al., *Nature,* 372:794–798, (1994).
Whitmarsh et al., *Science,* 269:403–407, (1995).
Xia et al., *Science,* 270:1326–1331, (1995).
Yan et al., *Nature,* 372:798–800, (1994).
Yashar et al., *Molecular and Cellular Biology,* 13:5738–5748, (1993).

*Primary Examiner*—Bradley L. Sisson
*Attorney, Agent, or Firm*—Fish & Richardson P.C.

[57] ABSTRACT

Disclosed are human mitogen-activated (MAP) kinase kinase isoforms (MKKs). MKKs mediate unique signal transduction pathways that activate human MAP kinases p38 and JNK, which result in activation of other factors, including activating transcription factor-2 (ATF2) and c-Jun. The pathways are activated by a number of factors, including cytokines and environmental stress. Methods are provided for identifying reagents that modulate MKK function or activity and for the use of such reagents in the treatment of MKK-mediated disorders.

4 Claims, 3 Drawing Sheets

```
                                                                                        71
MKK3       MSKPP----------APNPTPPRN------------LDSRTFITIG--------DRNFEVEADD
MKK4       MQGKRRALKLNFAN..FKSTARFTLN...GVQ.PHIERLRTHSIE.SGKLK.SP----EQHWDFT.E
MEK1       MPKKKP--TPIQLN.A-PDGSAVNGTSSAETNLEALQKKLEELE..EQQRKRLEAFLTQKQKVG.LKD..
MEK2       MLARRKPVL.PALTIN.TIAEGPSPTSEGASEANLVDLQKKLEELE..EQQKKRLEAFLTQKAKVG.LKD..
PBS2       <GTTPRTGNSNNS-NSGSSGGGLFANFSKYVDIKSGSLNFAGKLSL.SKG.DFSN---GSSSRITL.E
Consensus 142
MKK3       LVTISELGRGAYGVVEKVRHAQSGTIMAVKRIRATVNSQEQKRLLMDLDINMRTVDCFYTVTFYGALFREG
MKK4       .KDLG.I......S.N.MV.KP..Q........S..DEK...Q......VV..SS..P.I.Q........
MEK1       FEK.....A.NG...F.VS.KP..LV..R.L.HLEIKPAIRNQIIRE.QV-LHECNSP.I.G.....FYSD.
MEK2       FER.....A.NG...T.VQ.RP..L...R.L.HLEIKPAIRNQIIRE.QV-LHECNSP.I.G.....FYSD.
PBS2       .EFLD...H.N..N.S.VL.KPTNV..T.EV.LELDEAKFRQI..E.EV-LHKCNSP.I.D....F.I..
Consensus        E G G  G V K    H    MA K                                L       Y V FYGA   G 213
MKK3       DWICMELMD-TSLDKFYR---KVLDKNMTIPEDILGEIAVSIVRALEHLHSKLSVIHRDVKPSNVL-INK
MKK4       .C........S--..F....KYVYS...D--V...E...K.TLAT.K.N..KEN.KI....I......I.-LDR
MEK1       EIS...H..GG...Q--------.K.AGR...Q...KVSIAVIKG.TY.RE.HKIM........I.-V.S
MEK2       EIS...H..GG...Q--------.KEAKR...E...KVSIAVL.G.AY.RE.HQIM........I.-V.S
PBS2       A.YM...Y..GG....IYDESSEIGG-----.D.PQ.AF..NAVIHG.KE.KEQHNI........T.I.CSAN
Consensus                CME M   S  D            I E  L        L   L        L     HRD KP N L 284
MKK3       EGHVKMCDFGISGYLVDSVAKTMDAGCKPYMAPERINP-ELNQKGYNVKSDVWSLGITMIEMAILRFPY--
MKK4       S.NI.L....Q...I..R....R......D.-SASRQ.D.R..........LY.L.TG.....
MEK1       R.EI.L....V..Q.I.M.NSF-V.TRS..S......LQGTH----.S.Q..I..M.LSLIV..VG.Y.IPP
MEK2       R.EI.L....V..Q.I.M.NSF-V.TRS........LQGTH----.S.Q..I..M.LSLIV.L.VG.Y.IPP
PBS2       Q.T..L....V..N..A.L....NI..QS......KSLNPDRAT.T.Q..I....LSIL....LG.Y..PP
Consensus  G   K CDFG SG L  S A      G    YM PER          Y V SD WS G    E A R P 355
MKK3       ESWG-------------------------------------------TPFQQLKQVVEEPSPQLPAD---R
MKK4       PK.N-------------------------------------------SV.D.T...KGDP..SNSEERE
MEK1       PDAKELELMFGCQV-----EGDAAETPPRPRTPGRPLSSYGMDSRPPMAI.EL.DYI.N..P.K..SGV---
MEK2       PDAKELEAIFGRPVVDGEEGEPHSISPRPRPPGRPVSGHGMDSRPAMAI.EL.DYI.N..P.K..NGV----
PBS2       .TYD------------------------------------------NI.S..SAI.DG.P.R..S.---K
Consensus                                                              F   L V     P L 426
MKK3       FSPEFVDFTAQCLRKNPAERMSYLELMEHPFFTLHKTKKTDIAAFVK-------KILGEDS
MKK4       ...S.IN.VNL..T.DESK.PK.K..LK...ILMYEERAVEV.CY.C---------.DQMPATPSSPMYVD
MEK1       .L..Q..VNK..I......ADLKQ..V.A.IKRSDAEEV.F.GWLCSTIGLNQPSTPTHAAGV
MEK2       .T.D.QE.VNK...I......ADLKM.TN.T.IKRSEVEEV.F.GWLCKTLRLNQPGTPTRTA
PBS2       ..SDAQD.VSL..Q.I.ER.PT.AA.T..PWLVKYRNQDVHMSEYITERLERRN...R.RGENGLSKNVP>
Consensus   F    F    CL K       R        L        H
```

FIG. 1

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 189 amino acids
        ( B ) TYPE: amino acid
        ( C ) STRANDEDNESS: Not Relevant
        ( D ) TOPOLOGY: both ( i i ) MOLECULE TYPE: protein ( x i ) SEQUENCE DESCRIPTION: SEQ ID NO:1:

```
Met Gln Gly Lys Arg Lys Ala Leu Lys Leu Asn Phe Ala Asn Phe Lys
 1               5                  10                  15

Ser Thr Ala Arg Phe Thr Leu Asn Gly Asx Gln Pro His Ile Glu Arg
            20                  25                  30

Leu Arg Thr His Ser Ile Glu Ser Gly Lys Leu Lys Ser Pro Glu Gln
            35                  40                  45

His Trp Asp Phe Thr Glu Lys Asp Leu Gly Ile Ser Asn Met Val Lys
        50                  55                  60

Pro Gln Ser Asp Glu Lys Gln Val Val Ser Ser Pro Ile Gln Cys Ser
65                  70                  75                  80

Phe Lys Tyr Val Tyr Ser Asp Val Glu Lys Thr Leu Ala Thr Lys Asn
                    85                  90                  95

Lys Glu Asn Lys Ile Ile Ile Leu Asp Arg Ser Asn Ile Leu Gln Ile
            100                 105                 110

Arg Arg Asp Ser Ala Ser Arg Gln Asp Arg Leu Tyr Leu Thr Gly Pro
            115                 120                 125

Lys Asn Ser Val Asp Thr Lys Gly Asp Pro Ser Asn Ser Glu Glu Arg
    130                 135                 140

Glu Ser Ile Asn Val Asn Leu Thr Asp Glu Ser Lys Pro Lys Lys Leu
145                 150                 155                 160

Lys Ile Leu Met Tyr Glu Glu Arg Ala Val Glu Val Cys Tyr Cys Asp
                    165                 170                 175

Gln Met Pro Ala Thr Pro Ser Ser Pro Met Tyr Val Asp
            180                 185
```

( 2 ) INFORMATION FOR SEQ ID NO:2:

( i ) SEQUENCE CHARACTERISTICS:
        ( A ) LENGTH: 318 amino acids
        ( B ) TYPE: amino acid
        ( C ) STRANDEDNESS: Not Relevant
        ( D ) TOPOLOGY: both (i i) MOLECULE TYPE: protein (x i) SEQUENCE DESCRIPTION: SEQ ID NO:2:

| Met | Ser | Lys | Pro | Pro | Ala | Pro | Asn | Pro | Thr | Pro | Pro | Arg | Asn | Leu | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Arg | Thr | Phe | Ile | Thr | Ile | Gly | Asp | Arg | Asn | Phe | Glu | Val | Glu | Ala |
|     |     |     | 20  |     |     |     |     | 25  |     |     |     |     | 30  |     |     |

| Asp | Asp | Leu | Val | Thr | Ile | Ser | Glu | Leu | Gly | Arg | Gly | Ala | Tyr | Gly | Val |
|     |     | 35  |     |     |     |     | 40  |     |     |     |     | 45  |     |     |     |

| Val | Glu | Lys | Val | Arg | His | Ala | Gln | Ser | Gly | Thr | Ile | Met | Ala | Val | Lys |
|     | 50  |     |     |     |     | 55  |     |     |     |     | 60  |     |     |     |     |

| Arg | Ile | Arg | Ala | Thr | Val | Asn | Ser | Gln | Glu | Gln | Lys | Arg | Leu | Leu | Met |
| 65  |     |     |     |     | 70  |     |     |     |     | 75  |     |     |     |     | 80  |

| Asp | Leu | Asp | Ile | Asn | Met | Arg | Thr | Val | Asp | Cys | Phe | Tyr | Thr | Val | Thr |
|     |     |     |     | 85  |     |     |     |     | 90  |     |     |     |     | 95  |     |

| Phe | Tyr | Gly | Ala | Leu | Phe | Arg | Glu | Gly | Asp | Val | Trp | Ile | Cys | Met | Glu |
|     |     |     | 100 |     |     |     |     | 105 |     |     |     |     | 110 |     |     |

| Leu | Met | Asp | Thr | Ser | Leu | Asp | Lys | Phe | Tyr | Arg | Lys | Val | Leu | Asp | Lys |
|     |     | 115 |     |     |     |     | 120 |     |     |     |     | 125 |     |     |     |

| Asn | Met | Thr | Ile | Pro | Glu | Asp | Ile | Leu | Gly | Glu | Ile | Ala | Val | Ser | Ile |
|     | 130 |     |     |     |     | 135 |     |     |     |     | 140 |     |     |     |     |

| Val | Arg | Ala | Leu | Glu | His | Leu | His | Ser | Lys | Leu | Ser | Val | Ile | His | Arg |
| 145 |     |     |     |     | 150 |     |     |     |     | 155 |     |     |     |     | 160 |

| Asp | Val | Lys | Pro | Ser | Asn | Val | Leu | Ile | Asn | Lys | Glu | Gly | His | Val | Lys |
|     |     |     |     | 165 |     |     |     |     | 170 |     |     |     |     | 175 |     |

| Met | Cys | Asp | Phe | Gly | Ile | Ser | Gly | Tyr | Leu | Val | Asp | Ser | Val | Ala | Lys |
|     |     |     | 180 |     |     |     |     | 185 |     |     |     |     | 190 |     |     |

| Thr | Met | Asp | Ala | Gly | Cys | Lys | Pro | Tyr | Met | Ala | Pro | Glu | Arg | Ile | Asn |
|     |     | 195 |     |     |     |     | 200 |     |     |     |     | 205 |     |     |     |

| Pro | Glu | Leu | Asn | Gln | Lys | Gly | Tyr | Asn | Val | Lys | Ser | Asp | Val | Trp | Ser |
|     | 210 |     |     |     |     | 215 |     |     |     |     | 220 |     |     |     |     |

| Leu | Gly | Ile | Thr | Met | Ile | Glu | Met | Ala | Ile | Leu | Arg | Phe | Pro | Tyr | Glu |
| 225 |     |     |     |     | 230 |     |     |     |     | 235 |     |     |     |     | 240 |

| Ser | Trp | Gly | Thr | Pro | Phe | Gln | Gln | Leu | Lys | Gln | Val | Val | Glu | Glu | Pro |
|     |     |     |     | 245 |     |     |     |     | 250 |     |     |     |     | 255 |     |

| Ser | Pro | Gln | Leu | Pro | Ala | Asp | Arg | Glu | Ser | Pro | Glu | Phe | Val | Asp | Phe |
|     |     |     | 260 |     |     |     |     | 265 |     |     |     |     | 270 |     |     |

| Thr | Ala | Gln | Cys | Leu | Arg | Lys | Asn | Pro | Ala | Glu | Arg | Met | Ser | Tyr | Leu |
|     |     | 275 |     |     |     |     | 280 |     |     |     |     | 285 |     |     |     |

| Glu | Leu | Met | Glu | His | Pro | Phe | Phe | Thr | Leu | His | Lys | Thr | Lys | Lys | Thr |
|     | 290 |     |     |     |     | 295 |     |     |     |     | 300 |     |     |     |     |

| Asp | Ile | Ala | Ala | Phe | Val | Lys | Lys | Ile | Leu | Gly | Glu | Asp | Ser |
| 305 |     |     |     |     | 310 |     |     |     |     | 315 |     |     |     |

(2) INFORMATION FOR SEQ ID NO:3:

(i) SEQUENCE CHARACTERISTICS:
        (A) LENGTH: 273 amino acids
        (B) TYPE: amino acid
        (C) STRANDEDNESS: Not Relevant
        (D) TOPOLOGY: both (i i) MOLECULE TYPE: protein (x i) SEQUENCE DESCRIPTION: SEQ ID NO:3:

| Met | Pro | Lys | Lys | Lys | Pro | Thr | Pro | Ile | Gln | Leu | Asn | Ala | Pro | Asp | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

-continued

```
Ser  Ala  Val  Asn  Gly  Thr  Ser  Ser  Ala  Glu  Thr  Asn  Leu  Glu  Ala  Leu
               20                   25                        30

Gln  Lys  Lys  Leu  Glu  Glu  Leu  Glu  Glu  Gln  Gln  Arg  Lys  Arg  Leu  Glu
          35                        40                   45

Ala  Phe  Leu  Thr  Gln  Lys  Gln  Lys  Val  Gly  Leu  Lys  Asp  Phe  Glu  Lys
     50                        55                        60

Ala  Asn  Gly  Phe  Val  Ser  Lys  Pro  Leu  Val  Arg  Leu  His  Leu  Glu  Ile
65                       70                   75                             80

Lys  Pro  Ala  Ile  Arg  Asn  Gln  Ile  Ile  Arg  Glu  Gln  Val  Leu  His  Glu
                    85                        90                        95

Cys  Asn  Ser  Pro  Ile  Gly  Phe  Tyr  Ser  Asp  Glu  Ile  Ser  His  Gly  Gly
               100                      105                  110

Gln  Lys  Ala  Gly  Arg  Gln  Lys  Val  Ser  Ile  Ala  Val  Ile  Lys  Gly  Thr
               115                      120                  125

Tyr  Arg  Glu  His  Lys  Ile  Met  Ile  Val  Ser  Arg  Glu  Ile  Leu  Val  Gln
     130                      135                  140

Ile  Met  Asn  Ser  Phe  Val  Thr  Arg  Ser  Ser  Leu  Gln  Gly  Thr  His  Ser
145                      150                       155                       160

Gln  Ile  Met  Leu  Ser  Leu  Val  Val  Gly  Tyr  Ile  Pro  Pro  Pro  Asp  Ala
               165                      170                       175

Lys  Glu  Leu  Glu  Leu  Met  Phe  Gly  Cys  Gln  Val  Glu  Gly  Asp  Ala  Ala
               180                      185                       190

Glu  Thr  Pro  Pro  Arg  Pro  Arg  Thr  Pro  Gly  Arg  Pro  Leu  Ser  Ser  Tyr
          195                      200                  205

Gly  Met  Asp  Ser  Arg  Pro  Pro  Met  Ala  Ile  Glu  Leu  Asp  Tyr  Ile  Asn
     210                      215                  220

Pro  Lys  Ser  Gly  Val  Leu  Gln  Val  Asn  Lys  Ile  Ala  Asp  Leu  Lys  Gln
225                      230                       235                       240

Val  Ala  Ile  Lys  Arg  Ser  Asp  Ala  Glu  Glu  Val  Phe  Gly  Trp  Leu  Cys
               245                      250                       255

Ser  Thr  Ile  Gly  Leu  Asn  Gln  Pro  Ser  Thr  Pro  Thr  His  Ala  Ala  Gly
               260                      265                       270

Val
```

( 2 ) INFORMATION FOR SEQ ID NO:4:

( i ) SEQUENCE CHARACTERISTICS:
( A ) LENGTH: 274 amino acids
( B ) TYPE: amino acid
( C ) STRANDEDNESS: Not Relevant
( D ) TOPOLOGY: both ( i i ) MOLECULE TYPE: protein ( x i ) SEQUENCE DESCRIPTION: SEQ ID NO:4:

```
Met  Leu  Ala  Arg  Arg  Lys  Pro  Val  Leu  Pro  Ala  Leu  Thr  Ile  Asn  Thr
1                   5                        10                            15

Ile  Ala  Glu  Gly  Pro  Ser  Pro  Thr  Ser  Glu  Gly  Ala  Ser  Glu  Ala  Asn
               20                        25                        30

Leu  Val  Asp  Leu  Gln  Lys  Lys  Leu  Glu  Glu  Gln  Gln  Leu  Lys  Arg  Leu
               35                        40                        45

Glu  Ala  Phe  Leu  Thr  Gln  Lys  Ala  Lys  Val  Gly  Leu  Lys  Asp  Phe  Glu
          50                        55                        60

Arg  Ala  Asn  Gly  Thr  Val  Gln  Arg  Pro  Leu  Arg  Leu  His  Leu  Glu  Ile
65                       70                       75                            80

Lys  Pro  Ala  Ile  Arg  Asn  Gln  Ile  Ile  Arg  Glu  Gln  Val  Leu  His  Glu
                    85                        90                        95
```

```
Cys  Asn  Ser  Pro  Ile  Gly  Phe  Tyr  Ser  Asp  Glu  Ile  Ser  His  Gly  Gly
               100            105                      110

Gln  Lys  Glu  Ala  Lys  Arg  Glu  Lys  Val  Ser  Ile  Ala  Val  Leu  Gly  Ala
               115                 120                      125

Tyr  Arg  Glu  His  Gln  Ile  Met  Ile  Val  Ser  Arg  Glu  Ile  Leu  Val  Gln
     130                      135                      140

Ile  Met  Asn  Ser  Phe  Val  Thr  Arg  Ser  Leu  Gln  Gly  Thr  His  Ser  Gln
145                      150                      155                           160

Ile  Met  Leu  Ser  Leu  Val  Leu  Val  Gly  Tyr  Ile  Pro  Pro  Asp  Ala
                    165                      170                      175

Lys  Glu  Leu  Glu  Leu  Met  Phe  Gly  Cys  Gln  Val  Glu  Gly  Asp  Ala  Ala
               180                 185                      190

Glu  Thr  Pro  Pro  Arg  Pro  Arg  Thr  Pro  Gly  Arg  Pro  Leu  Ser  Ser  Tyr
          195                      200                 205

Gly  Met  Asp  Ser  Arg  Pro  Pro  Met  Ala  Ile  Glu  Leu  Asp  Tyr  Ile  Asn
     210                      215                      220

Pro  Lys  Ser  Gly  Val  Thr  Asp  Gln  Glu  Val  Asn  Lys  Ile  Ala  Asp  Leu
225                      230                      235                           240

Lys  Met  Thr  Asn  Thr  Ile  Lys  Arg  Ser  Glu  Val  Glu  Glu  Val  Phe  Gly
                    245                      250                      255

Trp  Leu  Cys  Lys  Thr  Leu  Arg  Leu  Asn  Gln  Pro  Gly  Thr  Pro  Thr  Arg
               260                      265                      270

Thr  Ala
```

( 2 ) INFORMATION FOR SEQ ID NO:5:

( i ) SEQUENCE CHARACTERISTICS:
      ( A ) LENGTH: 247 amino acids
      ( B ) TYPE: amino acid
      ( C ) STRANDEDNESS: Not Relevant
      ( D ) TOPOLOGY: both ( i i ) MOLECULE TYPE: protein ( x i ) SEQUENCE DESCRIPTION: SEQ ID NO:5:

```
Gly  Thr  Thr  Pro  Arg  Thr  Gly  Asn  Ser  Asn  Asn  Ser  Asn  Ser  Gly  Ser
1                   5                      10                          15

Ser  Gly  Gly  Gly  Gly  Leu  Phe  Ala  Asn  Phe  Ser  Lys  Tyr  Val  Asp  Ile
               20                      25                      30

Lys  Ser  Gly  Ser  Leu  Asn  Phe  Ala  Gly  Lys  Leu  Ser  Leu  Ser  Lys  Gly
          35                      40                      45

Asp  Phe  Ser  Asn  Gly  Ser  Ser  Arg  Ile  Thr  Leu  Glu  Glu  Phe  Leu
     50                      55                      60

Asp  His  Asn  Asn  Ser  Val  Leu  Lys  Pro  Thr  Asn  Val  Thr  Glu  Val  Leu
65                       70                      75                           80

Glu  Leu  Asp  Glu  Ala  Lys  Phe  Arg  Gln  Ile  Glu  Glu  Val  Leu  His  Lys
               85                      90                      95

Cys  Asn  Ser  Pro  Ile  Asp  Phe  Ile  Ala  Tyr  Met  Tyr  Gly  Gly  Ile  Tyr
               100                     105                     110

Asp  Glu  Ser  Ser  Glu  Ile  Gly  Gly  Asp  Pro  Gln  Ala  Phe  Asn  Ala  Val
               115                     120                     125

Ile  His  Gly  Lys  Glu  Lys  Glu  Gln  His  Asn  Ile  Thr  Ile  Cys  Ser  Ala
     130                     135                     140

Asn  Gln  Thr  Leu  Val  Asn  Ala  Leu  Asn  Ile  Gln  Ser  Lys  Ser  Leu  Asn
145                     150                     155                           160

Pro  Asp  Arg  Ala  Thr  Thr  Gln  Ile  Leu  Ser  Ile  Leu  Leu  Gly  Tyr  Pro
```

-continued

```
                                165                                 170                                 175
        Pro    Thr    Tyr    Asp    Asn    Ile    Ser    Ser    Ala    Ile    Asp    Gly    Pro    Arg    Ser    Ser
                             180                          185                          190

Lys    Ser    Asp    Ala    Gln    Asp    Val    Ser    Leu    Gln    Ile    Glu    Arg    Pro    Thr    Ala
                      195                          200                          205

Ala    Thr    Pro    Trp    Leu    Val    Lys    Tyr    Arg    Asn    Gln    Asp    Val    His    Met    Ser
               210                          215                          220

Glu    Tyr    Ile    Thr    Glu    Arg    Leu    Glu    Arg    Arg    Asn    Arg    Arg    Gly    Glu    Asn
        225                          230                          235                                        240

Gly    Leu    Ser    Lys    Asn    Val    Pro
                                    245
```

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: both
        ( D ) TOPOLOGY: both ( i i ) MOLECULE TYPE: DNA (genomic)

( x i ) SEQUENCE DESCRIPTION: SEQ ID NO:6:

TTYTAYGGNG CNTTYTTYAT HGA                                                              23

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: both ( i i ) MOLECULE TYPE: cDNA ( x i ) SEQUENCE DESCRIPTION: SEQ ID NO:7:

ATBCTYTCNG GNGCCATKTA                                                              20

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: both ( i i ) MOLECULE TYPE: protein ( x i ) SEQUENCE DESCRIPTION: SEQ ID NO:8:

```
        Asp    Tyr    Lys    Asp    Asp    Asp    Lys
        1                           5
```

CYTOKINE-, STRESS-, AND ONCOPROTEIN-ACTIVATED HUMAN PROTEIN KINASE KINASES

STATEMENT AS TO FEDERALLY SPONSORED RESEARCH

This invention was made in part with National Cancer Institute research grant CA 58396. The Federal government has certain rights in the invention.

BACKGROUND OF THE INVENTION

This invention relates to protein kinases.

Mitogen-activated protein (MAP) kinases are important mediators of signal transduction from the cell surface to the nucleus. Multiple MAP kinases have been described in yeast including SMK1, HOG1, NPK1, FUS3, and KSS1. In mammals, the MAP kinases identified are extracellular signal-regulated MAP kinase (ERK), c-Jun amino-terminal kinase (JNK), and p38 kinase (Davis (1994) Trends Biochem. Sci. 19:470). These MAP kinase isoforms are activated by dual phosphorylation on threonine and tyrosine.

Activating Transcription Factor-2 (ATF2), ATFa, and cAMP Response Element Binding Protein (CRE-BPa) are related transcription factors that bind to similar sequences located in the promoters of many genes (Ziff (1990) Trends in Genet. 6:69). The binding of these transcription factors leads to increased transcriptional activity. ATF2 binds to several viral proteins, including the oncoprotein Ela (Liu and Green (1994) Nature 368:520), the hepatitis B virus X protein (Maguire et al. (1991) Science 252:842), and the human T cell leukemia virus 1 tax protein (Wagner and Green (1993) Science 262:395). ATF2 also interacts with the tumor suppressor gene product Rb (Kim et al. (1992) Nature 358:331), the high mobility group protein HMG(I)Y (Du et al. (1993) Cell 74:887), and the transcription factors nuclear NF-xB (Du et al. (1993) Cell 74:887) and c-Jun (Benbrook and Jones (1990) Oncogene 5:295).

SUMMARY OF THE INVENTION

We have identified and isolated a new group of human mitogen-activated protein kinase kinases (MKKs). The MKK isoforms described herein, MKK3 and MKK4 (including MKK4-α, -β, and -γ) have serine, threonine, and tyrosine kinase activity, and specifically phosphorylate the human MAP kinase p38 at $Thr^{180}$ and $Tyr^{182}$. The MKK4 isoforms also phosphorylate the human MAP kinases JNK (including JNK1 and JNK2) at $Thr^{183}$ and $Tyr^{185}$.

Accordingly, the invention features a substantially pure human MKK polypeptide having serine, threonine, and tyrosine kinase activity that specifically phosphorylates human p38 MAP kinase. MKK3 has the amino acid sequence of SEQ ID NO:2.

The invention further features a substantially pure human MKK polypeptide having serine, threonine, and tyrosine kinase activity that specifically phosphorylates human p38 MAP kinase and JNK. MKK4 isoform MKK4-α has the amino acid sequence of SEQ ID NO:1.

As used herein, the term "mitogen-activating protein kinase kinase" or "MKK" means a protein kinase which possesses the characteristic activity of phosphorylating and activating a human mitogen-activating protein kinase. Examples of MKKs include MKK3, which specifically phosphorylates and activates p38 MAP kinase at $Thr^{180}$ and $Tyr^{182}$, and MKK4 isoforms which specifically phosphorylate and activate p38 MAP kinase at $Thr^{180}$ and $Tyr^{182}$, and JNK at $Thr^{183}$ and $Tyr^{185}$.

The invention includes the specific p38 MKKs disclosed, as well as closely related MKKs which are identified and isolated by the use of probes or antibodies prepared from the polynucleotide and amino acid sequences disclosed for the MKKs of the invention. This can be done using standard techniques, e.g., by screening a genomic, cDNA, or combinatorial chemical library with a probe having all or a part of the nucleic acid sequences of the disclosed MKKs. The invention further includes synthetic polynucleotides having all or part of the amino acid sequence of the MKKs herein described.

The term "polypeptide" means any chain of amino acids, regardless of length or post-translational modification (e.g., glycosylation or phosphorylation), and includes natural proteins as well as synthetic or recombinant polypeptides and peptides.

The term "substantially pure," when referring to a polypeptide, means a polypeptide that is at least 60%, by weight, free from the proteins and naturally-occurring organic molecules with which it is naturally associated. A substantially pure human MKK polypeptide is at least 75%, more preferably at least 90%, and most preferably at least 99%, by weight, human MKK polypeptide. A substantially pure human MKK can be obtained, for example, by extraction from a natural source; by expression of a recombinant nucleic acid encoding a human MKK polypeptide, or by chemically synthesizing the protein. Purity can be measured by any appropriate method, e.g., column chromatography, polyacrylamide gel electrophoresis, or HPLC analysis.

In one aspect, the invention features isolated and purified polynucleotides which encode the MKKs of the invention.

As used herein, "polynucleotide" refers to a nucleic acid sequence of deoxyribonucleotides or ribonucleotides in the form of a separate fragment or a component of a larger construct. DNA encoding portions or all of the polypeptides of the invention can be assembled from cDNA fragments or from oligonucleotides that provide a synthetic gene which can be expressed in a recombinant transcriptional unit. Polynucleotide sequences of the invention include DNA, RNA, and cDNA sequences, and can be derived from natural sources or synthetic sequences synthesized by methods known to the art.

As used herein, an "isolated" polynucleotide is a polynucleotide that is not immediately contiguous (i.e., covalently linked) with either of the coding sequences with which it is immediately contiguous (i.e., one at the 5' end and one at the 3' end) in the naturally-occurring genome of the organism from which the polynucleotide is derived. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences.

The isolated and purified polynucleotide sequences of the invention also include polynucleotide sequences that hybridize under stringent conditions to the polynucleotide sequences specified herein. The term "stringent conditions" means hybridization conditions that guarantee specificity between hybridizing polynucleotide sequences, such as those described herein, or more stringent conditions. One skilled in the art can select posthybridization washing conditions, including temperature and salt concentrations, which reduce the number of nonspecific hybridizations such that only highly complementary sequences are identified (Sambrook et al. (1989) in *Molecular Cloning*, 2ed.; Cold Spring Harbor Laboratory Press, Cold Spring Harbor, N.Y., hereby specifically incorporated by reference).

The isolated and purified polynucleotide sequences of the invention also include sequences complementary to the polynucleotide encoding MKK (antisense sequences). Antisense nucleic acids are DNA or RNA molecules that are complementary to at least a portion of a specific mRNA molecule (Weintraub (1990) Scientific American 262:40). The invention includes all antisense polynucleotides capable of inhibiting production of MKK polypeptides. In the cell, the antisense nucleic acids hybridize to the corresponding mRNA, forming a double-stranded molecule. Antisense oligomers of about 15 nucleotides are preferred, since they are easily synthesized and introduced into a target MKK-producing cell. The use of antisense methods to inhibit the translation of genes is known in the art, and is described, e.g., in Marcus-Sakura Anal. Biochem., 172:289 (1988).

In addition, ribozyme nucleotide sequences for MKK are included in the invention. Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech (1988) J. Amer. Med. Assn. 260:3030). A major advantage of this approach is that, because they are sequence-specific, only mRNAs with particular sequences are inactivated.

There are two basic types of ribozymes namely, tetrahymena-type (Hasselhoff (1988) Nature 334:585) and "hammerhead"-type. Tetrahymena-type ribozymes recognize sequences which are four bases in length, while "hammerhead"-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating a specific mRNA species, and 18-base recognition sequences are preferable to shorter recognition sequences.

The MKK polypeptides can also be used to produce antibodies that are immunoreactive or bind epitopes of the MKK polypeptides. Accordingly, one aspect of the invention features antibodies to the MKK polypeptides of the invention. The antibodies of the invention include polyclonal antibodies which consist of pooled monoclonal antibodies with different epitopic specificities, as well as distinct monoclonal antibody preparations. Monoclonal antibodies are made from antigen-containing fragments of the MKK polypeptide by methods known in the art (See, for example, Kohler et al. (1975) Nature 256:495).

The term "antibody" as used herein includes intact molecules as well as fragments thereof, such as Fa, F(ab')$_2$, and Fv, which are capable of binding the epitopic determinant. Antibodies that bind MKK polypeptides can be prepared using intact polypeptides or fragments containing small peptides of interest as the immunizing antigen. The polypeptide or peptide used to immunize an animal can be derived from translated CDNA or chemically synthesized, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The invention also features methods of identifying subjects at risk for MKK-mediated disorders by measuring activation of the MKK signal transduction pathway. Activation of the MKK signal transduction pathway can be determined by measuring MKK synthesis; activation of MKK isoforms; activation of MKK substrates p38 or JNK isoforms; or activation of p38 and JNK substrates such as ATF2, ATFa, CRE-BPa, and c-Jun. The term "JNK" or "JNK isoforms" includes both JNK1 and JNK2. The term "MKK substrate" as used herein include MKK substrates, as well as MKK substrate substrates, e.g., p38, JNK, ATF2, and c-Jun.

In one embodiment, activation of the MKK signal transduction pathway is determined by measuring activation of the MKK signal transduction pathway substrates p38, JNK isoforms, ATF2, or c-Jun. MKK activity is measured by the rate of substrate phosphorylation as determined by quantitation of the rate of [$^{32}$]P incorporation. The specificity of MKK substrate phosphorylation can be tested by measuring p38 and JNK activation, or by employing mutated p38 and JNK molecules that lack the sites of MKK phosphorylations. Altered phosphorylation of the substrate relative to control values indicates alteration of the MKK signal transduction pathway, and increased risk in a subject of an MKK-mediated disorder. MKK activation of p38 and JNK can be detected in a coupled assay with the MKK signal transduction substrate ATF2, or related compounds such as ATFa and CRE-BPa. Activation can also be detected with the substrate c-Jun. When ATF2 is included in the assay, it is present as an intact protein or as a fragment of the intact protein, e.g., the activation domain (residues 1-109, or a portion thereof). ATF2 is incubated with a test sample in which MKK activity is to be measured and [γ-$^{32}$P]ATP, under conditions sufficient to allow the phosphorylation of ATF2. ATF2 is then isolated and the amount of phosphorylation quantitated. In a specific embodiment, ATF2 is isolated by immunoprecipitation, resolved by SDS-PAGE, and detected by autoradiography.

In another embodiment, activation of the MKK signal transduction pathway is determined by measuring the level of MKK expression in a test sample. In a specific embodiment, the level of MKK expression is measured by Western blot analysis. The proteins present in a sample are fractionated by gel electrophoresis, transferred to a membrane, and probed with labeled antibodies to MKK. In another specific embodiment, the level of MKK expression is measured by Northern blot analysis. Polyadenylated [poly (A)+] mRNA is isolated from a test sample. The mRNA is fractionated by electrophoresis and transferred to a membrane. The membrane is probed with labeled MKK cDNA. In another embodiment, MKK expression is measured by quantitative PCR applied to expressed mRNA.

The MKKs of the invention are useful to screen reagents that modulate MKK activity. MKKs are activated by phosphorylation. Accordingly, in one aspect, the invention features methods for identifying a reagent which modulates MKK activity, by incubating MKK with the test reagent and measuring the effect of the test reagent on MKK synthesis, phosphorylation, function, or activity. In one embodiment, the test reagent is incubated with MKK and [$^{32}$]P-ATP, and the rate of MKK phosphorylation determined, as described above. In another embodiment, the test reagent is incubated with a cell transfected with an MKK polynucleotide expression vector, and the effect of the test reagent on MKK transcription is measured by Northern blot analysis, as described above. In a further embodiment, the effect of the test reagent on MKK synthesis is measured by Western blot analysis using an antibody to MKK. In still another embodiment, the effect of a reagent on MKK activity is measured by incubating MKK with the test reagent, [$^{32}$]P-

ATP, and a substrate in the MKK signal transduction pathway, including one or more of p38, JNK, and ATF2. The rate of substrate phosphorylation is determined as described above.

The term "modulation of MKK activity" includes inhibitory or stimulatory effects. The invention is particularly useful for screening reagents that inhibit MKK activity. Such reagents are useful for the treatment or prevention of MKK-mediated disorders, for example, inflammation and oxidative damage.

The invention further features a method of treating a MKK-mediated disorder by administering to a subject in need thereof an effective dose of a therapeutic reagent that inhibits the activity of MKK.

By the term "MKK-mediated disorder" is meant a pathological condition resulting, at least in part, from excessive activation of an MKK signal transduction pathway.

The MKK signal transduction pathways are activated by several factors, including inflammation and stress. MKK-mediated disorders include, for example, ischemic heart disease, burns due to heat or radiation (UV, X-ray, γ, β, etc.), kidney failure, liver damage due to oxidative stress or alcohol, respiratory distress syndrome, septic shock, rheumatoid arthritis, autoimmune disorders, and other types of inflammatory diseases.

As used herein, the term "therapeutic reagent" means any compound or molecule that achieves the desired effect on an MKK-mediated disorder when administered to a subject in need thereof.

MKK-mediated disorders further include proliferative disorders, particularly disorders that are stress-related. Examples of stress-related MKK-mediated proliferative disorders are psoriasis, acquired immune deficiency syndrome, malignancies of various tissues of the body, including malignancies of the skin, bone marrow, lung, liver, breast, gastrointestinal system, and genito-urinary tract. Preferably, therapeutic reagents inhibit the activity or expression of MKK inhibit cell growth or cause apoptosis.

A therapeutic reagent that "inhibits MKK activity" interferes with a MKK-mediated signal transduction pathway. For example, a therapeutic reagent can alter the protein kinase activity of MKK, decrease the level of MKK transcription or translation, e.g., an antisense polynucleotide able to bind MKK mRNA, or suppress MKK phosphorylation of p38, JNK, or ATF2, thus disrupting the MKK-mediated signal transduction pathway. Examples of such reagents include antibodies that bind specifically to MKK polypeptides, and fragments of MKK polypeptides that competitively inhibit MKK polypeptide activity.

A therapeutic reagent that "enhances MKK activity" supplements a MKK-mediated signal transduction pathway. Examples of such reagents include the MKK polypeptides themselves, which can be administered in instances where the MKK-mediated disorder is caused by underexpression of the MKK polypeptide. In addition, portions of DNA encoding an MKK polypeptide can be introduced into cells that underexpress an MKK polypeptide.

A "therapeutically effective amount" is an amount of a reagent sufficient to decrease or prevent the symptoms associated with the MKK-mediated disorder.

Therapeutic reagents for treatment of MKK-mediated disorders identified by the method of the invention are administered to a subject in a number of ways known to the art, including parenterally by injection, infusion, sustained-release injection or implant, intravenously, intraperitoneally, intramuscularly, subcutaneously, or transdermally. Epidermal disorders and disorders of the epithelial tissues are treated by topical application of the reagent. The reagent is mixed with other compounds to improve stability and efficiency of delivery (e.g., liposomes, preservatives, or dimethyl sulfoxide (DMSO)). Polynucleotide sequences, including antisense sequences, can be therapeutically administered by techniques known to the art resulting in introduction into the cells of a subject suffering from the MKK-mediated disorder. These methods include the use of viral vectors (e.g., retrovirus, adenovirus, vaccinia virus, or herpes virus), colloid dispersions, and liposomes.

The materials of the invention are ideally suited for the preparation of a kit for the detection of the level or activity of MKK. Accordingly, the invention features a kit comprising an antibody that binds MKK, or a nucleic acid probe that hybridizes to a MKK polynucleotide, and suitable buffers. The probe or monoclonal antibody can be labeled to detect binding to a MKK polynucleotide or protein. In a preferred embodiment, the kit features a labeled antibody to MKK.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION

The drawings will first be described.
Drawings FIG. 1 is a comparison of the amino acid sequences of MKK3 (SEQ ID NO:2), MKK4-α(SEQ ID NO:1), the human MAP kinase kinases MEK1 (SEQ ID NO:3) and MEK2 (SEQ ID NO:4), and the yeast HOG1 MAP kinase kinase PBS2 (SEQ ID NO:5). MKK3 and MKK4 sequences were compared with the PILE-UP program (version 7.2; Wisconsin Genetics Computer Group). The protein sequences are presented in single letter code [A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp, and Y, Tyr]. The PBS2 sequence is truncated at both the $NH_2$—(<) and COOH—(>) termini. Gaps introduced into the sequences to optimize the alignment are illustrated by a dash. Identical residues are indicated by a period. The sites of activating phosphorylation in MEK are indicated by asterisks.

Figure 2:
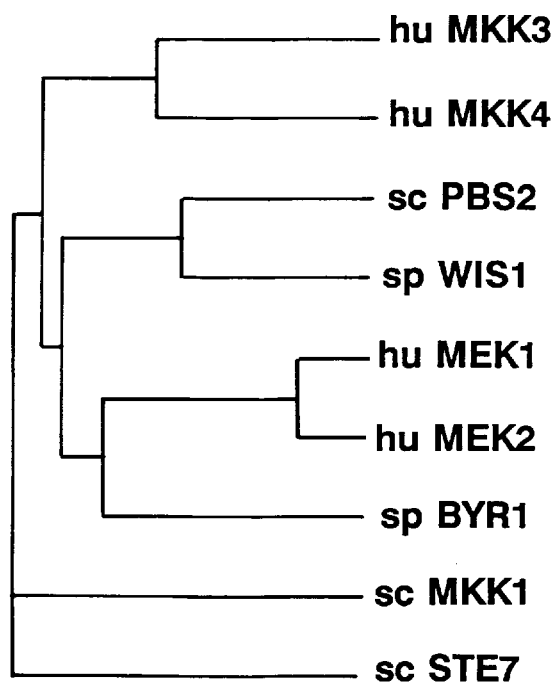

FIG. 2 is a dendrogram showing the relation between members of the human and yeast MAP kinase kinases. The dendrogram was created by the unweighted pair-group method with the use of arithmetic averages (PILE-UP program). The human (hu) MAP kinase kinases MEK1, MEK2, MKK3, and MKK4; the *Saccharomyces cerevisiae* (sc) MAP kinase kinases PBS2, MKK1, and STE7; and the *Saccharomyces pombe* (sp) MAP kinase kinases WIS1 and BYR1 are presented.

Figure 3:
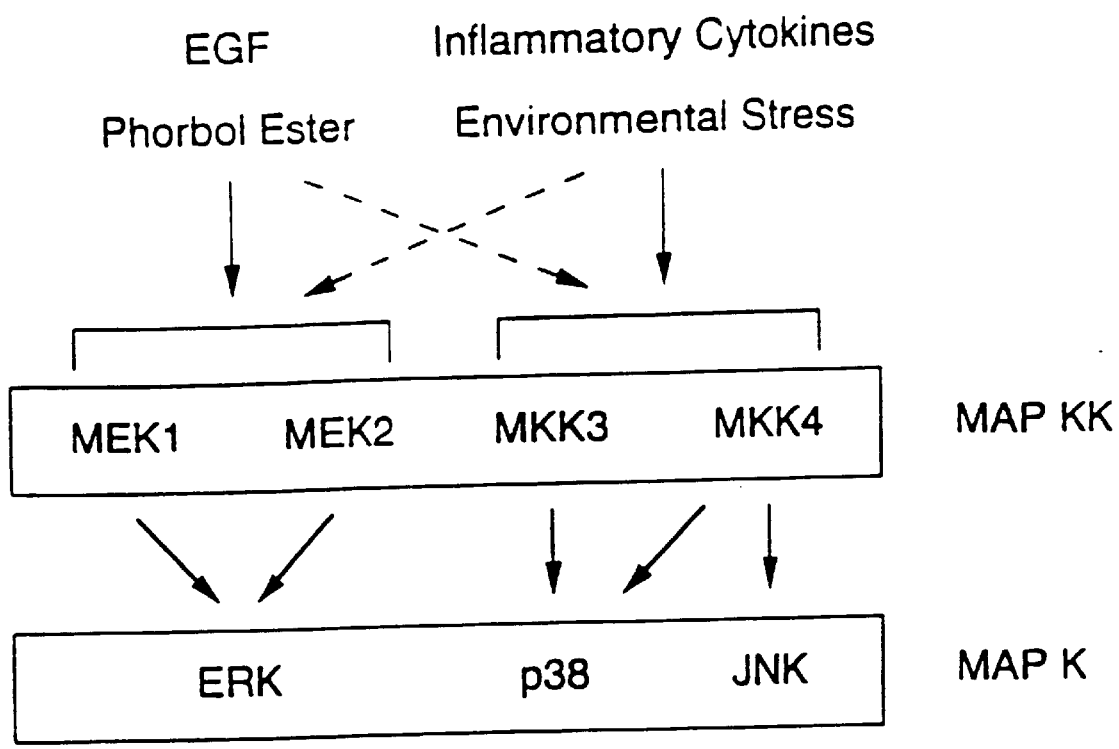

FIG. 3 is a schematic representation of the ERK, p38, and JNK signal transduction pathways. MEK1 and MEK2 are activators of the ERK subgroup of MAP kinase. MKK3 and MKK4 are activators of the p38 MAP kinase. MKK4 is identified as an activator of both the p38 and JNK subgroups of MAP kinase.

HUMAN MITOGEN-ACTIVATED PROTEIN KINASE KINASES

The human MAP kinase kinases MKK3 and MKK4 (MKK3/4) described herein mediate the transduction of specific signals from the cell surface to the nucleus along specific pathways. These signal transduction pathways are initiated by factors such as cytokines, UV radiation, osmotic shock, and oxidative stress. Activation of MKK3/4 results in activation of the MAP kinases p38 (MKK3/4) and JNK (MKK4). p38 and JNK in turn activate a group of related transcription factors such as ATF2, ATFa, and CRE-BPa. These transcription factors in turn activate expression of specific genes. For example, ATF2 in known to activate expression of human T cell leukemia virus 1 (Wagner and Green (1993) Science 262:395), transforming growth factor-b2 (Kim et al. (1992) supra), interferon-$\beta$ (Du et al. (1993) Cell 74:887), and E-selectin (DeLuca et al. (1994) J. Biol. Chem. 269:19193). In addition, ATF2 is implicated in the function of a T cell-specific enhancer (Georgopoulos et al. (1992) Mol. Cell. Biol. 12:747).

The isolation of human MKKs is described in Example 1 and in Dérijard et al. (1995) Science 267:682-685, hereby specifically incorporated by reference. Distinctive regions of the yeast PBS2 sequence were used to design polymerase chain reaction (PCR) primers. Amplification of human brain mRNA with these primers resulted in the formation of specific products which were cloned into a plasmid vector and sequenced. Two different complementary DNAs (cDNAs) that encoded human protein kinases were identified: one encoding a 36 kD protein (MKK3), and one encoding a 44 kD protein (MKK4). MKK4 includes 3 isoforms that vary slightly at the $NH_2$-terminal, identified as $\alpha$, $\beta$, and $\gamma$. The amino acid sequences of MKK3 (SEQ ID NO:2), and MKK4-$\alpha$(SEQ ID NO:1). Other human MKK3 and MKK4 isoforms that exist can be identified by the method described in Example 1.

The expression of these human MKK isoforms was examined by Northern (RNA) blot analysis of mRNA isolated from eight adult human tissues (Example 2). Both protein kinases were found to be widely expressed in human tissues, with the highest expression seen in skeletal muscle tissue.

The substrate specificity of MKK3 was investigated in an in vitro phosphorylation assay with recombinant epitope-tagged MAP kinases (JNK1, p38, and ERK2) as substrates (Example 3). MKK3 phosphorylated p38, but did not phosphorylate JNK1 or ERK2. Phosphoaminoacid analysis of p38 demonstrated the presence of a phosphothreonine and phosphotyrosine. Mutational analysis of p38 demonstrated that replacement of phosphorylation sites $Thr^{180}$ and $Tyr^{182}$ with Ala and Phe, respectively, blocked p38 phosphorylation. These results establish that MKK3 functions in vitro as a p38 MAP kinase kinase.

Studies of the in vitro substrate specificity of MKK4 are described in Example 4. MKK4 incubated with [$\gamma$-$^{32}$P]ATP, and JNK1, p38, or ERK2 was found to phosphorylate both p38 and JNK1. MKK4 activation of JNK and p38 was also studied by incubating MKK4 with wild-type or mutated JNK1 or p38. The p38 substrate ATF2 was included in each assay. MKK4 was found to exhibit less autophosphorylation than MKK3. MKK4 was also found to be a substrate for activated MAP kinase. Unlike MKK3, MKK4 was also found to activate JNK1. MKK4 incubated with wild-type JNK1, but not mutated JNK1, resulted in increased phosphorylation of ATF2. These results establish that MKK4 is a p38 MAP kinase kinase that also phosphorylates the JNK subgroup of MAP kinases.

In vivo activation of p38 by UV-stimulated MKK3 is described in Example 5. Cells expressing MKK3 were exposed in the presence or absence of UV radiation. MKK3 was isolated by immunoprecipitation and used for protein kinase assays with the substrates p38 or JNK. ATF2 was included in some assays as a substrate for p38 and JNK. MKK3 from non-activated cultured COS cells caused a small amount of phosphorylation of p38 MAP kinase, resulting from basal activity of MKK3. MKK3 from UV-irradiated cells caused increased phosphorylation of p38 MAP kinase, but not of JNK1. An increase in p38 activity was also detected in assays in which ATF2 was included as a substrate. These results establish that MKK3 is activated by UV radiation.

The effect of expression of MKK3 and MKK4 on p38 activity was examined in COS-1 cells (Example 6). Cells were transfected with a vector encoding p38 and a MEK1, MKK3, or MKK4. Some of the cells were also exposed to EGF or UV radiation. p38 was isolated by immunoprecipitation and assayed for activity with [$\gamma$-$^{32}$P]ATP and ATF2. The expression of the ERK activator MEK1 did not alter p38 phosphorylation of ATF2. In contrast, expression of MKK3 or MKK4 caused increased activity of p38 MAP kinase. The activation of p38 caused by MKK3 and MKK4 was similar to that observed in UV-irradiated cells, and was much greater than that detected in EGF-treated cells. These in vitro results provide evidence that MKK3 and MKK4 activate p38 in vivo.

A series of experiments was conducted to examine the potential regulation of ATF2 by JNK1. These experiments are described in Gupta et al. (1995) Science 267:389–393, hereby specifically incorporated by reference. The effect of UV radiation on ATF2 phosphorylation was investigated in COS-1 cells transfected with and without epitope-tagged JNK1 (Example 7). Cells were exposed to UV radiation, and JNK1 and JNK2 visualized by in-gel protein kinase assay with the substrate ATF2. JNK1 and JNK2 were detected in transfected and non-transfected cells exposed to UV radiation; however, JNK1 levels were higher in the transfected cells. These results demonstrate that ATF2 is a substrate for the JNK1 and JNK2 protein kinases, and that these protein kinases are activated in cells exposed to UV light.

The site of JNK1 phosphorylation of ATF2 was examined by deletion analysis (Example 8). Progressive $NH_2$-terminal domain deletion GST-ATF2 fusion proteins were generated, and phosphorylation by JNK1 isolated from UV-irradiated cells was examined. The results showed that JNK1 requires the presence of ATF2 residues 1-60 for phosphorylation of the $NH_2$-terminal domain of ATF2.

The ATF2 residues required for binding of JNK1 were similarly examined. JNK1 was incubated with immobilized ATF2, unbound JNK1 was removed by extensive washing, and bound JNK1 was detected by incubation with [$\gamma$-$^{32}$P] ATP. Results indicate that residues 20 to 60 of ATF2 are required for binding and phosphorylation by JNK1. A similar binding interaction between ATF2 and the 55 kD JNK2 protein kinase has also been observed.

Phosphorylation by JNK1 was shown to reduce the electrophoretic mobility of ATF2 (Example 9). Phosphoamino acid analysis of the full-length ATF2 molecule (residues 1-505 ) demonstrated that JNK phosphorylated both Thr and Ser residues. The major sites of Thr and Ser phosphorylation were located in the $NH_2$ and COOH terminal domains, respectively. The $NH_2$-terminal sites of phosphorylation were identified as $Thr^{69}$ and $Thr^{71}$ by phosphopeptide mapping and mutational analysis. These sites of Thr phosphorylation are located in a region of ATF2 that is distinct from the sub-domain required for JNK binding (residues 20 to 60).

The reduced electrophoretic mobility seen with phosphorylation of ATF2 was investigated further (Example 10). JNK1 was activated in CHO cells expressing JNK1 by treatment with UV radiation, pro-inflammatory cytokine interleukin-1 (IL-1), or serum. A decreased electrophoretic mobility of JNK1-activated ATF2 was observed in cells treated with UV radiation and IL-1. Smaller effects were seen after treatment of cells with serum. These results indicate that ATF2 is an in vivo substrate for JNK1.

The effect of UV radiation on the properties of wild-type (Thr$^{69,71}$) and phosphorylation-defective (Ala$^{69,71}$) ATF2 molecules was investigated (Example 11). Exposure to UV caused a decrease in the electrophoretic mobility of both endogenous and over-expressed wild-type ATF2. This change in electrophoretic mobility was associated with increased ATF2 phosphorylation. Both the electrophoretic mobility shift and increased phosphorylation were blocked by the replacement of Thr$^{69}$ and Thr$^{71}$ with Ala in ATF2. This mutation also blocked the phosphorylation of ATF2 on Thr residues in vivo.

Transcriptional activities of fusion proteins consisting of the GAL4 DNA binding domain and wild-type or mutant ATF2 were examined (Example 12). Point mutations at Thr$^{69}$ and/or Thr$^{71}$ of ATF2 significantly decreased the transcriptional activity of ATF2 relative to the wild-type molecule, indicating the physiological relevance of phosphorylation at these sites for activity.

The binding of JNK1 to the NH$_2$-terminal activation domain of ATF2 (described in Example 8) suggested that a catalytically inactive JNK1 molecule could function as a dominant inhibitor of the wild-type JNK1 molecule. This hypothesis was investigated by examining the effect of a catalytically inactive JNK1 molecule on ATF2 function (Example 13). A catalytically-inactive JNK1 mutant was constructed by replacing the sites of activating Thr$^{183}$ and Tyr$^{185}$ phosphorylation with Ala and Phe, respectively (Ala$^{183}$, Phe$^{185}$, termed "dominant-negative"). Expression of wild-type JNK1 caused a small increase in serum-stimulated ATF2 transcriptional activity. In contrast, dominant-negative JNK1 inhibited both control and serum-stimulated ATF2 activity. This inhibitory effect results from the non-productive binding of the JNK1 mutant to the ATF2 activation domain, effectively blocking ATF2 phosphorylation.

The tumor suppressor gene product Rb binds to ATF2 and increases ATF2-stimulated gene expression (Kim et al. (1992) Nature 358:331). Similarly, the adenovirus oncoprotein E1A associates with the DNA binding domain of ATF2 and increases ATF2-stimulated gene expression by a mechanism that requires the NH$_2$-terminal activation domain of ATF2 (Liu and Green (1994) Nature 368:520). ATF2 transcriptional activity was investigated with the luciferase reporter gene system in control, Rb-treated, and E1A-treated cells expressing wild-type or mutant ATF2 molecules (Example 14). Rb and E1A were found to increase ATF2-stimulated gene expression of both wild-type and mutant ATF2. However, mutant ATF2 caused a lower level of reporter gene expression than did wild-type ATF2. Together, these results indicate a requirement for ATF2 phosphorylation (on Thr$^{69}$ and Thr$^{71}$) plus either Rb or E1A for maximal transcriptional activity. Thus, Rb and E1A act in concert with ATF2 phosphorylation to control transcriptional activity.

A series of experiments were conducted to examine the action of p38 activation and to establish the relationship of the p38 MAP kinase pathway to the ERK and JNK signal transduction pathways (Raingeaud et al. (1995) J. Biol. Chem. 270:7420, hereby specifically incorporated by reference). Initially, the substrate specificity of p38 was investigated by incubating p38 with proteins that have been demonstrated to be substrates for the ERK and/or JNK groups of MAP kinases (Example 15). We examined the phosphorylation of MBP (Erickson et al. (1990) J. Biol. Chem. 265:19728), EGF-R (Northwood et al. (1991) J. Biol. Chem. 266:15266), cytoplasmic phospholipase A$_2$ (cPLA$_2$) (Lin et al. (1993) Cell 72:269), c-Myc (Alvarez et al. (1991) J. Biol. Chem. 266:15277), IκB, c-Jun, and wild-type (Thr$^{69,71}$) or mutated (Ala$^{69,71}$) ATF2. p38 phosphorylated MBP and EGF-R, and to a lesser extent IκB, but not the other ERK substrates, demonstrating that the substrate specificity of p38 differs from both the ERK and JNK groups of MAP kinases. Wild-type ATF2, but not mutated ATF2 (Ala$^{69,71}$), was found to be an excellent p38 substrate.

The phosphorylation of ATF2 by p38 was associated with an electrophoretic mobility shift of ATF2 during polyacrylamide gel electrophoresis. We tested the hypothesis that p38 phosphorylates ATF2 at the same sites as JNK1 by replacing Thr$^{69}$ and Thr$^{71}$ with Ala (Ala$^{69,71}$). It was found that p38 did not phosphorylate mutated ATF2, which demonstrates that p38 phosphorylates ATF2 within the NH$_2$-terminal activation domain on Thr$^{69}$ and Thr$^{71}$.

A comparison of the binding of JNK and p38 to ATF2 was conducted by incubating extracts of cells expressing JNK1 or p38 with epitope alone (GST) or GST-ATF2 (residues 1-109 containing the activation domain) (Example 16). Bound protein kinases were detected by Western blot analysis. The results demonstrate that both p38 and JNK bind to the ATF2 activation domain.

EGF and phorbol ester are potent activators of the ERK signal transduction pathway (Egan and Weinberg (1993) Nature 365:781), causing maximal activation of the ERK sub-group of MAP kinases. These treatments, however, cause only a small increase in JNK protein kinase activity (Dérijard et al. (1994) supra; Hibi et al. (1993) supra). The effects of EGF or phorbol esters, as well UV radiation, osmotic shock, interleukin-1, tumor necrosis factor, and LPS, on p38 activity were all tested (Example 17). Significantly, EGF and phorbol ester caused only a modest increase in p38 protein kinase activity, whereas environmental stress (UV radiation and osmotic shock) caused a marked increase in the activity of both p38 and JNK. Both p38 and JNK were activated in cells treated with pro-inflammatory cytokines (TNF and IL-1) or endotoxic LPS. Together, these results indicate that p38, like JNK, is activated by a stress-induced signal transduction pathway.

ERKs and JNKs are activated by dual phosphorylation within the motifs Thr-Glu-Tyr and Thr-Pro-Tyr, respectively. In contrast, p38 contains the related sequence Thr-Gly-Tyr. To test whether this motif is relevant to the activation of p38, the effect of the replacement of Thr-Gly-Tyr with Ala-Gly-Phe was examined (Example 18). The effect of UV radiation on cells expressing wild-type (Thr$^{180}$,Tyr$^{182}$) or mutant p38 (Ala$^{180}$,Phe$^{182}$) was studied. Western blot analysis using an anti-phosphotyrosine antibody demonstrated that exposure to UV radiation caused an increase in the Tyr phosphorylation of p38. The increased Tyr phosphorylation was confirmed by phosphoaminoacid analysis of p38 isolated from [γ-$^{32}$P]phosphate-labeled cells. This analysis also demonstrated that UV radiation caused increased Thr phosphorylation of p38. Significantly, the increased phosphorylation on Thr$^{180}$ and Tyr$^{182}$ was blocked by the Ala$^{180}$/Phe $^{182}$ mutation. This result demonstrates that UV radiation causes increased activation of p38 by dual phosphorylation.

It has recently been demonstrated that ERK activity is regulated by the mitogen-induced dual specificity phosphatases MKP1 and PAC1 (Ward et al. (1994) Nature 367:651). The activation of p38 by dual phosphorylation (Example 18) raises the possibility that p38 may also be regulated by dual specificity phosphatases. We examined the effect of MKP1 and PAC1 on p38 MAP kinase activation (Example 19). Cells expressing human MKP1 and PAC1 were treated with and without UV radiation, and p38 activity measured. The expression of PAC1 or MKP1 was found to inhibit p38 activity. The inhibitory effect of MKP1 was greater than PAC1. In contrast, cells transfected with a catalytically inactive mutant phosphatase (mutant PAC1 Cys$^{257}$/Ser) did not inhibit p38 MAP kinase. These results demonstrate that p38 can be regulated by dual specificity phosphatases PAC1 and MKP1.

The sub-cellular distribution of p38 MAP kinase was examined by indirect immunofluorescence microscopy (Example 20). Epitope-tagged p38 MAP kinase was detected using the M2 monoclonal antibody. Specific staining of cells transfected with epitope-tagged p38 MAP kinase was observed at the cell surface, in the cytoplasm, and in the nucleus. Marked changes in cell surface and nuclear p38 MAP kinase were not observed following UV irradiation, but an increase in the localization of cytoplasmic p38 MAP kinase to the perinuclear region was detected.

A series of experiments were conducted to study the activation of JNK by hyper-osmotic media (Example 21). These experiments were reported by Galcheva-Gargova et al. (1994) Science 265:806, hereby specifically incorporated by reference. CHO cells expressing epitope-tagged JNK1 were incubated with 0–1000 mM sorbitol, and JNK1 activity measured in an immune complex kinase assay with the substrate c-Jun. Increased JNK1 activity was observed in cells incubated 1 hour with 100 mM sorbitol. Increased JNK1 activity was observed within 5 minutes of exposure to 300 mM sorbitol. Maximal activity was observed 15 to 30 minutes after osmotic shock with a progressive decline in JNK1 activity at later times. The activation of JNK by osmotic shock was studied in cells expressing wild-type (Thr$^{183}$, Tyr$^{185}$) or mutated (Ala$^{183}$, Phe$^{185}$) JNK1. JNK1 activity was measured after incubation for 15 minutes with or without 300 mM sorbitol. Cells expressing wild-type JNK1 showed increased JNK1 activity, while cells expressing mutated JNK1 did not. These results demonstrate that the JNK signal transduction pathway is activated in cultured mammalian cells exposed to hyper-osmotic media.

The results of the above-described experiments are illustrated in FIG. 3, which diagrams the ERK, p38, and JNK MAP kinase signal transduction pathways. ERKs are potently activated by treatment of cells with EGF or phorbol esters. In contrast, p38 is only slightly activated under these conditions (Example 15). However, UV radiation, osmotic stress, and inflammatory cytokines cause a marked increase in p38 activity. This difference in the pattern of activation of ERK and p38 suggests that these MAP kinases are regulated by different signal transduction pathways. The molecular basis for the separate identity of these signal transduction pathways is established by the demonstration that the MAP kinase kinases that activate ERK (MEK1 and MEK2) and p38 (MKK3 and MKK4) are distinct.

MKK isoforms are useful for screening reagents which modulate MKK activity. Described in the Use section following the examples are methods for identifying reagents capable of inhibiting or activating MKK activity.

The discovery of human MKK isoforms and MKK-mediated signal transduction pathways is clinically significant for the treatment of MKK-mediated disorders. One use of the MKK isoforms is in a method for screening reagents able to inhibit or prevent the activation of the MKK-MAP kinase-ATF2 pathways.

The following examples are meant to illustrate, not limit, the invention.

EXAMPLE 1

MKK Protein Kinases

The primary sequences of MKK3 and MKK4 were deduced from the sequence of cDNA clones isolated from a human fetal brain library.

The primers TTYTAYGGNGCNTTYTTYATHGA (SEQ ID NO:6) and ATBCTYTCNGGNGCCATKTA (SEQ ID NO:7) were designed based on the sequence of PBS2 (Brewster et al. (1993) Science 259:1760; Maeda et al. (1994) Nature 369:242). The primers were used in a PCR reaction with human brain mRNA as template. Two sequences that encoded fragments of PBS2-related protein kinases were identified. Full-length human cDNA clones were isolated by screening of a human fetal brain library (Derijard et al. (1994) supra). The cDNA clones were examined by sequencing with an Applied Biosystems model 373A machine. The largest clones obtained for MKK3 (2030 base pairs (bp)) and MKK4 (3576 bp) contained the entire coding region of these protein kinases.

The primary structures of MKK3 and MKK4 are shown in FIG. 1 (SEQ ID NO:2; SEQ ID NO:1; An in-frame termination codon is located in the 5' untranslated region of the MKK3 CDNA, but not in the 5' region of the MKK4 cDNA. The MKK4 protein sequence presented starts at the second in-frame initiation codon.

These sequences were compared to those of the human MAP kinase kinases MEK1 (SEQ ID NO:3) and MEK2 (SEQ ID NO:4) (Zheng and Guan (1993) J. Biol. Chem 268:11435) and of the yeast MAP kinase kinase PBS2 (SEQ ID NO:5) (Boguslawaski and Polazzi (1987) Proc. Natl. Acad. Sci. USA 84:5848) (FIG. 1). The identity and similarity of the kinases with human MKK3 (between subdomains I and XI) were calculated with the BESTFIT program (version 7.2; Wisconsin Genetics Computer Group) (percent of identity to percent of similarity): MEK1, 41%/63%; MEK2, 41%/62%; MKK4, 52%/73%; and PBS2, 40%/59%). The identity and similarity of the kinases with human MKK4 were calculated to be as follows (percent of identity to percent of similarity): MEK1, 44%/63%; MEK2, 45%/61%; MKK3, 52%/73%; and PBS2, 44%/58%. The CDNA sequences of MKK3 and MKK4 have been deposited in GenBank with accession numbers L36719 and L36870, respectively.

EXAMPLE 2

Expression of MKK3 and MKK4 mRNA in Adult Human Tissue

Northern blot analysis was performed with polyadenylated [poly(A)+] mRNA (2 $\mu$g) isolated from human heart, brain, placenta, lung, liver, muscle, kidney, and pancreas tissues. The mRNA was fractionated by denaturing agarose gel electrophoresis and was transferred to a nylon membrane. The blot was probed with the MKK3 and MKK4 cDNA labeled by random priming with [α-$^{32}$P]ATP (deoxyadenosine triphosphate) (Amersham International PLC). MKK3 and MKK4 were expressed in all tissues examined; the highest expression of MKK3 and MKK4 was found in skeletal muscle tissue.

The relation between members of the human and yeast MAP kinase kinase group is presented as a dendrogram (FIG. 2). MKK3/4 form a unique subgroup of human MAP kinase kinases.

EXAMPLE 3

In Vitro Phosphorylation of p38 MAP kinase by MKK3

GST-JNK1, and GST-ERK2 have been described (Dérijard et al. (1994) supra; Gupta et al. (1995) Science 267:389; Wartmann and Davis (1994) J. Biol. Chem. 269:6695, each herein specifically incorporated by reference). GST-p38 MAP kinase was prepared from the expression vector pGSTag (Dressier et al. (1992) Biotechniques 13:866) and a PCR fragment containing the coding region of the p38 MAP kinase cDNA. GST-MKK3 and MKK4 were prepared with pGEX3X (Pharmacia-LKB Biotechnology) and PCR fragments containing the coding region of the MKK3 and MKK4 cDNAs. The GST fusion proteins were purified by affinity chromatography with the use of GSH-agarose (Smith and Johnson (1988) Gene 67:31). The expression vectors pCMV-Flag-JNK1 and pCMV-MEK1 have been described (Dérijard et al. (1994) supra; Wartmann and Davis (1994) supra). The plasmid pCMV-Flag-p38 MAP kinase was prepared with the expression vector pCMV5 (Andersson et al. (1989) J. Biol. Chem. 264:8222) and the p38 MAP kinase cDNA. The expression vectors for MKK3 and MKK4 were prepared by subcloning of the cDNAs into the polylinker of pCDNA3 (Invitrogen). The Flag epitope (Asp-Tyr-Lys-Asp-Asp-Asp-Asp-Lys (SEQ ID NO:8); Immunex, Seattle, Wash.) was inserted between codons 1 and 2 of the kinases by insertional overlapping PCR (Ho et al. (1989) Gene 77:51).

Protein kinase assays were performed in kinase buffer (25 mM 4-(2-hydroxyethyl)-1-piperazineethansulfonic acid, pH 7.4, 25 mM β-glycerophosphate, 25 mM MgCl$_2$, 2 mM dithiothreitol, and 0.1 mM orthovanadate). Recombinant GST-MKK3 was incubated with [γ-$^{32}$P]ATP and buffer, GST-JNK1, GST-p38 MAP kinase, or GST-ERK2. The assays were initiated by the addition of 1 μg of substrate proteins and 50 μM [γ-$^{32}$P]ATP (10 Ci/mmol) in a final volume of 25 μl. The reactions were terminated after 30 minutes at 25° C. by addition of Laemmli sample buffer. The phosphorylation of the substrate proteins was examined after SDS-polyacrylamide gel electrophoresis (SDS-PAGE) by autoradiography. Phosphoaminoacid analysis was performed by partial acid hydrolysis and thin-layer chromatography (Dérijard et al. (1994) supra; Alvarez et al. (1991) J. Biol. Chem. 266:15277). Autophosphorylation of MKK3 was observed in all groups. MKK3 phosphorylated p38 MAP kinase, but not JNK1 or ERK2.

A similar insertional overlapping PCR procedure was used to replace Thr$^{180}$ and Tyr$^{182}$ of p38, with Ala and Phe, respectively. The sequence of all plasmids was confirmed by automated sequencing on an Applied Biosystems model 373A machine. GST-MKK3 was incubated with [γ-$^{32}$P]ATP and buffer, wild-type GST-p38 MAP kinase (TGY), or mutated GST-p38 MAP kinase (AGF). The phosphorylated proteins were resolved by SDS-PAGE and detected by autoradiography. Only phosphorylation of wild-type p38 was observed.

EXAMPLE 4

In Vitro Phosphorylation and Activation of JNK and p38 MAP Kinase by MKK4

Protein kinase assays were conducted as described in Example 3. Recombinant GST-MKK4 was incubated with [γ-$^{32}$P]ATP and buffer, GST-JNK1, GST-p38 MAP kinase, or GST-ERK2. JNK1 and p38 were phosphorylated, as was MKK4 incubated with JNK1 and p38.

GST-MKK4 was incubated with [γ-$^{32}$p ]ATP and buffer, wild-type JNK1 (Thr$^{183}$, Tyr$^{185}$), or mutated GST-JNK1 (Ala 183, Phe$^{185}$). The JNK1 substrate ATF2 (Gupta et al. (1995) supra) was included in each incubation. ATF2 was phosphorylated in the presence of MKK4 and wild-type JNK1. The results establish that MKK4 phosphorylates and activates both p38 and JNK1.

EXAMPLE 5

Phosphorylation and Activation of p38 MAP Kinase by UV-stimulated MKK3

Epitope-tagged MKK3 was expressed in COS-1 cells maintained in Dulbecco's modified Eagle's medium supplemented with fetal bovine serum (5%)(Gibco-BRL). The cells were transfected with the lipofectamine reagent according to the manufacturer's recommendations (Gibco-BRL) and treated with UV radiation or EGF as described (Dérijard et al. (1994) supra).

The cells were exposed in the absence and presence of UV-C (40 J/m$^2$). The cells were solubilized with lysis buffer (20 mM tris, pH 7.4, 1% TRINTON®X-100 (Aldrich, 1996–97 catalog number 23,210.3), 10% glycerol, 137 mM NaCl, 2 mM EDTA, 25 mM β-glycerophosphate, 1 mM Na orthovanadate, 1 mM phenylmethylsulfonyl fluoride, and leupeptin (10 μg/ml)) and centrifuged at 100,000×g for 15 minutes at 4° C. MKK3 was isolated by immunoprecipitation. The epitope-tagged protein kinases were incubated for 1 hour at 4° C. with the M2 antibody to the Flag epitope (IBI-Kodak) bound to protein G-Sepharose (Pharmacia-LKB Biotechnology). The immunoprecipitates were washed twice with lysis buffer and twice with kinase buffer.

Protein kinase assays were conducted with the substrate GST-p38 MAP kinase or JNK1. ATF2 was included in some assays. Basal levels of MKK3 phosphorylation of p38 MAP kinase were observed. UV-irradiation resulted in increased phosphorylation of p38 MAP kinase, but not of JNK1. The increased p38 MAP kinase activity resulted in increased phosphorylation of ATF2.

EXAMPLE 6

Activation of p38 MAP Kinase in Cells Expressing MKK3 and MKK4

COS-1 cells were transfected with epitope-tagged p38 MAP kinase, together with an empty expression vector or an expression vector encoding MEK1, MKK3, or MKK4. Some of the cultures were exposed to UV radiation (40 J/m$^2$) or treated with 10 nM EGF. p38 MAP kinase was isolated by immunoprecipitation with M2 monoclonal antibody, and the protein kinase activity was measured in the immunecomplex with [γ-$^{32}$p]ATP and ATF2 as substrates. The product of the phosphorylation reaction was visualized after SDS-PAGE by autoradiography. ATF2 was not phosphorylated in the control MEK1, or EGF-treated groups, but was phosphorylated in the MKK3, MKK4, and UV-irradiated groups. MKK3 and MKK4 phosphorylation of ATF2 was similar to that seen with p38 MAP kinase isolated from UV-irradiated cells.

EXAMPLE 7

Phosphorylation of ATF2 by JNK1 and JNK2

COS-1 cells were maintained in Dulbecco's modified Eagle's medium supplemented with bovine serum albumin (5%) (Gibco-BRL). Metabolic labeling with [$^{32}$P] was performed by incubation of cells for 3 hours in phosphate-free modified Eagle's medium (Flow Laboratories Inc.) supplemented with [$^{32}$P] orthophosphate (2 mCi/ml) (Dupont-NEN). COS-1 cells were transfected without (Mock) and with epitope-tagged JNK1 (JNK1). Plasmid expression vectors encoding the JNK1 cDNA have previously been described (Dérijard et al. (1994) Cell 76:1025, herein specifically incorporated by reference). Plasmid DNA was transfected into COS-1 cells by the lipofectamine method (Gibco-BRL). After 48 hours of incubation, some cultures were exposed to 40 J/m$^2$ UV radiation and incubated for 1 hour at 37° C.

Cells were lysed in 20 mM Tris, pH 7.5, 25 mM β-glycerophosphate, 10% glycerol, 1% Triton®X-100, 0.5% (w/v) deoxycholate, 0.1% (w/v) SDS, 0.137 M NaCl, 2 mM pyrophosphate, 1 mM orthovanadate, 2 mM EDTA, 10 μg/ml leupeptin, 1 mM PMSF. Soluble extracts were prepared by centrifugation in a microfuge for 20 minutes at 4° C. JNK1 immunoprecipitates were also prepared by reaction with a rabbit antiserum prepared with recombinant JNK1 as an antigen.

In-gel protein kinase assays were performed with cell lysates and JNK1 immunoprecipitates after SDS-PAGE by renaturation of protein kinases, polymerization of the substrate (GST-ATF2, residues1-505) in the gel, and incubation with [γ-$^{32}$P]ATP (Dérijard et al. (1994) supra). The incorporation of [$^{32}$P]phosphate was visualized by autoradiography and quantitated with a Phosphorimager and ImageQuant software (Molecular Dynamics Inc., Sunnyvale, Calif.). The cell lysates demonstrate the presence of 46 kD and 55 kD protein kinases that phosphorylate ATF2 in extracts prepared from UV-irradiated cells. The 46 kD and 55 kD protein kinases were identified as JNK1 and JNK2, respectively.

EXAMPLE 8

Binding of JNK1 to ATF2 and Phosphorylation of the NH$_2$-Terminal Activation Domain The site of JNK1 phosphorylation of ATF2 was investigated by generation of progressive NH$_2$-terminal domain deletions of ATF2. Plasmid expression vectors encoding ATF2 (pECE-ATF2) (Liu and Green (1994) and (1990)), have been described. Bacterial expression vectors for GST-ATF2 fusion proteins were constructed by sub-cloning ATF2 cDNA fragments from a polymerase chain reaction (PCR) into pGEX-3X (Pharmacia-LKB Biotechnology Inc.). The sequence of all constructed plasmids was confirmed by automated sequencing with an Applied Biosystems model 373A machine. The GST-ATF2 proteins were purified as described (Smith and Johnson (1988) Gene 67:31), resolved by SDS-PAGE and stained with Coomassie blue. GST-ATF2 fusion proteins contained residues 1-505, 1-349, 350-505, 1-109, 20-109, 40-109, and 60-109.

The phosphorylation of GST-ATF2 fusion proteins by JNK1 isolated from UV-irradiated cells was examined in an immunocomplex kinase assay. Immunecomplex kinase assays were performed with Flag epitope-tagged JNK1 and the monoclonal antibody M2 (IBI-Kodak) as described by Dérijard et al. (1994) supra). Immunecomplex protein kinase assays were also performed with a rabbit antiserum prepared with recombinant JNK1 as an antigen. The cells were solubilized with 20 mM Tris, pH 7.5, 10% glycerol, 1% Triton®X-100, 0.137 M NaCl, 25 mM β-glycerophosphate, 2 mM EDTA, 1 mM orthovanadate, 2 mM pyrophosphate, 10 μg/ml leupeptin, and 1 mM PMSF. JNK1 was immunoprecipitated with protein G-Sepharose bound to a rabbit polyclonal antibody to JNK or the M2 monoclonal antibody to the Flag epitope. The beads were washed three times with lysis buffer and once with kinase buffer (20 mM Hepes, pH 7.6, 20 mM MgCl$_2$, 25 mM β-glycerophosphate, 100 μM Na orthovanadate, 2 mM dithiothreitol). The kinase assays were performed at 25° C. for 10 minutes with 1 μg of substrate, 20 μM adenosine triphosphate and 10 μCi of [γ-$^{32}$P]ATP in 30μl of kinase buffer. The reactions were terminated with Laemmli sample buffer and the products were resolved by SDS-PAGE (10% gel). JNK1 phosphorylates GST-ATF2 fusion proteins containing residues 1-505, 1-349, 1-109, 20-109, and 40-109, but not 60-109. These results indicate that the presence of ATF2 residues 1-60 are required for phosphorylation by JNK.

The binding of immobilized GST-ATF2 fusion proteins was examined in a solid-phase kinase assay as described by Hibi et al. (1993) Genes Dev. 7:2135, herein specifically incorporated by reference. JNK1 from UV-irradiated cells was incubated with GST-ATF2 fusion proteins bound to GSH-agarose. The agarose beads were washed extensively to remove the unbound JNK1. Phosphorylation of the GST-ATF2 fusion proteins by the bound JNK1 protein kinase was examined by addition of [γ-$^{32}$P]ATP. JNK1 bound GST-ATF2 fusion proteins containing residues 1-505, 1-349, 1-109, 20-109, and 40-109, indicating that the presence of residues 20-60 were required for binding of JNK1 to ATF2.

EXAMPLE 9

Phosphorylation of the NH$_2$-terminal Activation Domain of ATF2 on Thr$^{69}$ and Thr$^{71}$ by JNK1

The effect of UV radiation on the properties of wild-type (Thr$^{69,71}$) and phosphorylation-defective (Ala$^{69,71}$) ATF2 molecules was examined. Mock-transfected and JNK1-transfected COS cells were treated without and with 40 J/m$^2$ UV radiation. The epitope-tagged JNK1 was isolated by immunoprecipitation with the M2 monoclonal antibody. The phosphorylation of GST-ATF2 (residues 1 to 109) was examined in an immunocomplex kinase assay as described above. The GST-ATF2 was resolved from other proteins by SDS-PAGE and stained with Coomassie blue. The phosphorylation of GST-ATF2 was detected by autoradiography. JNK1-transfected cells, but not mock-transfected cells, phosphorylated ATF2. JNK1 phosphorylation of ATF2 was greater in cells exposed to UV radiation. Phosphorylation of ATF2 by JNK1 was associated with a decreased electrophoretic mobility.

In a separate experiment, GST fusion proteins containing full-length ATF2 (residues 1 to 505), an NH$_2$-terminal fragment (residues 1 to 109), and a COOH-terminal fragment (residues 95 to 505) were phosphorylated with JNK1 and the sites of phosphorylation analyzed by phosphoamino acid analysis. The methods used for phosphopeptide mapping and phosphoamino acid analysis have been described (Alvarez et al. (1991) J. Biol. Chem. 266:15277). The horizontal dimension of the peptide maps was electrophoresis and the vertical dimension was chromatography. The NH$_2$-terminal sites of phosphorylation were identified as Thr$^{69}$ and Thr$^{71}$ by phosphopeptide mapping and mutational analysis. Site-directed mutagenesis was performed as described above, replacing Thr$^{69}$ and Thr$^{71}$ with Ala. Phosphorylation of mutated ATF2 was not observed.

EXAMPLE 10

Reduced Electrophoretic Mobility of JNK-Activated ATF2

CHO cells were maintained in Ham's F12 medium supplemented with 5% bovine serum albumin (Gibco-BRL). Cells were labeled and transfected with JNK1 as described above. CHO cells were treated with UV-C (40 J/m$^2$), IL-1α (10 ng/ml) (Genzyme), or fetal bovine serum (20%) (Gibco-BRL). The cells were incubated for 30 minutes at 37° C. prior to harvesting. The electrophoretic mobility of ATF2 after SDS-PAGE was examined by protein immuno-blot analysis. A shift in ATF2 electrophoretic mobility was observed in cells treated with UV, IL-1, and serum. These results indicate that JNK1 activation is associated with an electrophoretic mobility shift of ATF2, further suggesting that ATF2 is an in vivo substrate for JNK1.

EXAMPLE 11

Increased ATF2 Phosphorylation After Activation of JNK

COS-1 cells were transfected without (control) and with an ATF2 expression vector (ATF2), as described above (Hai et al. (1989) supra). The effect of exposure of the cells to 40 J/m$^2$ UV-C was examined. After irradiation, the cells were incubated for 0 or 30 minutes (control) or 0, 15, 30, and 45 minutes (ATF2) at 37° C. and then collected. The electrophoretic mobility of ATF2 during SDS-PAGE was examined by protein immuno-blot analysis as described above. The two electrophoretic mobility forms of ATF2 were observed in ATF2-transfected cells, but not in control cells.

The phosphorylation state of wild-type (Thr$^{69,71}$) ATF2 and mutated (Ala$^{69,71}$) ATF2 was examined in cells labeled with [$^{32}$]P, treated without and with 40 J/m$^2$ UV-C, and then incubated at 37° C. for 30 minutes (Hai et al. (1989) supra). The ATF2 proteins were isolated by immunoprecipitation and analyzed by SDS-PAGE and autoradiography. The phosphorylated ATF2 proteins were examined by phosphoamino acid analysis as described above. Both forms of ATF2 contained phosphoserine, but only wild-type ATF2 contained phosphothreonine.

Tryptic phosphopeptide mapping was used to compare ATF2 phosphorylated in vitro by JNK1 with ATF2 phosphorylated in COS-1 cells. A map was also prepared with a sample composed of equal amounts of in vivo and in vitro phosphorylated ATF2 (Mix). Mutation of ATF2 at Thr$^{69}$ and Thr$^{71}$ resulted in the loss of two tryptic phosphopeptides in maps of ATF2 isolated from UV-irradiated cells. These phosphopeptides correspond to mono- and bis-phosphorylated peptides containing Thr69 and Thr$^{71}$. Both of these phosphopeptides were found in maps of ATF2 phosphorylated by JNK1 in vitro.

EXAMPLE 12

Inhibition of ATF2-Stimulated Gene Expression by Mutation of the Phosphorylation Sites Thr$^{69}$ and Thr$^{71}$ A fusion protein consisting of ATF2 and the GAL4 DNA binding domain was expressed in CHO cells as described above. The activity of the GAL4-ATF2 fusion protein was measured in co-transfection assays with the reporter plasmid pG5ElbLuc (Seth et al. (1992) J. Biol. Chem. 267:24796, hereby specifically incorporated by reference). The reporter plasmid contains five GAL4 sites cloned upstream of a minimal promoter element and the firefly luciferase gene. Transfection efficiency was monitored with a control plasmid that expresses β-galactosidase (pCH110; Pharmacia-LKB Biotechnology). The luciferase and β-galactosidase activity detected in cell extracts was measured as the mean activity ratio of three experiments (Gupta et al. (1993) Proc. Natl. Acad. Sci. USA 90:3216, hereby specifically incorporated by reference). The results, shown in Table 1, demonstrate the importance of phosphorylation at Thr$^{69}$ and Thr$^{71}$ for transcriptional activity.

TABLE 1

INHIBITION OF ATF-2 STIMULATED GENE EXPRESSION BY MUTATION OF THE PHOSPHORYLATION SITES THR$^{69,71}$

| PROTEIN | LUCIFERASE ACTIVITY (Light Units/OD) |
|---|---|
| GAL4 | 45 |
| GAL4-ATF2 (wild type) | 320,000 |
| GAL4-ATF2 (Ala$^{69}$) | 24,000 |
| GAL4-ATF2 (Ala$^{71}$) | 22,000 |
| GAL4-ATF2 (Ala$^{69,71}$) | 29,000 |
| GAL4-ATF2 (Glu$^{69}$) | 27,000 |

EXAMPLE 13

Effect of Dominant-Negative JNK1 Mutant on ATF2 Function

The luciferase reporter plasmid system was used to determine the effect of point mutations at the ATF2 phosphorylation sites Thr$^{69}$ and Thr$^{71}$ in serum-treated CHO cells transfected with wild-type (Thr$^{183}$, Tyr$^{185}$) or mutant (Ala$^{183}$, Phe$^{185}$) JNK1. Control experiments were done with mock-transfected cells. The CHO cells were serum-starved for 18 hours and then incubated without or with serum for 4 hours. Expression of wild-type ATF2 caused a small increase in serum-stimulated ATF2 transcriptional activity. In contrast, mutant JNK1 inhibited both control and serum-stimulated ATF2 activity.

EXAMPLE 14

Effect of Tumor Suppressor Gene Product Rb and Adenovirus Oncoprotein E1A on ATF2-Stimulated Gene Expression The effect of expression of the Rb tumor suppressor gene product and adenovirus oncoprotein E1A on ATF2 transcriptional activity were investigated with a luciferase reporter plasmid and GAL4-ATF2 (residues 1-505), as described above. Cells were transfected with wild-type (Thr$^{69,71}$) or mutated (Ala$^{69,71}$) ATF2. No effect of Rb or E1A on luciferase activity was detected in the absence of GAL4-ATF2. Rb and E1A were found to increase ATF2-stimulated gene expression of both wild-type and mutated ATF2. However, mutated ATF2 caused a lower level of reporter gene expression than did wild-type ATF2. These results indicate a requirement for ATF2 phosphorylation (on Thr$^{69}$ and Thr$^{71}$) plus either Rb or E1A for maximal transcriptional activity.

EXAMPLE 15

Substrate Specificity of p38 MAP Kinase

Substrate phosphorylation by p38 MAP kinase was examined by incubation of bacterially-expressed p38 MAP kinase with IκB, cMyc, EGF-R, cytoplasmic phospholipase $A_2$ (cPLA$_2$), c-Jun, and mutated ATF2 (Thr$^{69,71}$) and ATP[γ-$^{32}$P] (Raingeaud et al. (1995) J. Biol. Chem 270:7420, herein specifically incorporated by reference). GST-IκB was provided by Dr D. Baltimore (Massachusetts Institute of Technology). GST-cMyc (Alvarez et al. (1991) J. Biol. Chem. 266:15277), GST-EGF-R (residues 647-688) (Koland et al. (1990) Biochem. Biophys. Res. Commun. 166:90), and GST-c-Jun (Dérijard et al. (1994) supra) have been described. The phosphorylation reaction was terminated after 30 minutes by addition of Laemmli sample buffer. The phosphorylated proteins were resolved by SDS-PAGE and detected by autoradiography. The rate phosphorylation of the substrate proteins was quantitated by PhosphorImager (Molecular Dynamics Inc.) analysis. The relative phosphorylation of ATF2, MBP, EGF-R, and IKB was 1.0, 0.23, 0.04, and 0.001, respectively.

EXAMPLE 16

Binding of p38 MAP Kinase to ATF2

Cell extracts expressing epitope-tagged JNK1 and p38 MAP kinase were incubated with a GST fusion protein containing the activation domain of ATF2 (residues 1-109) immobilized on GSH agarose. The supernatant was removed and the agarose was washed extensively. Western blot analysis of the supernatant and agarose-bound fractions was conducted as follows: proteins were fractionated by SDS-PAGE, electrophoretically transferred to an Immobilon-P membrane, and probed with monoclonal antibodies to phosphotyrosine (PY20) and the Flag epitope (M2). Immunocomplexes were detected using enhanced chemiluminescence (Amersham International PLC). Control experiments were performed using immobilized GST.

EXAMPLE 17 p38 MAP Kinase and JNK1 Activation by Pro-Inflammatory Cytokines and Environmental Stress The effect of phorbol ester, EGF, UV radiation, osmotic stress, IL-1, tumor necrosis factor (TNF), and LPS on p38 MAP kinase and JNK1 activity were measured in immunecomplex protein kinase assays using ATP[γ-$^{32}$P] and ATF2 as substrates. TNFα and IL-1α were from Genzyme Corp. Lipolysaccharide (LPS) was isolated from lyophilized *Salmonella minesota* Re595 bacteria as described (Mathison et a. (1988) J. Clin. Invest. 81:1925). Phorbol myristate acetate was from Sigma. EGF was purified from mouse salivary glands (Davis (1988) J. Biol. Chem. 263:9462). Kinase assays were performed using immunoprecipitates of p38 and JNK. The immunocomplexes were washed twice with kinase buffer (described above), and the assays initiated by the addition of 1 μg of ATF2 and 50 μM [γ-$^{32}$P]ATP (10 Ci/mmol) in a final volume of 25 μl. The reactions were terminated after 30 minutes at 30° C. by addition of Laemmli sample buffer. The phosphorylation of ATF2 was examined after SDS-PAGE by autoradiography, and the rate of ATF2 phosphorylation quantitated by PhosphorImager analysis.

The results are shown in Table 2. Exposure of HeLa cells to 10 nM phorbol myristate acetate very weakly activated p38 and JNK1. Similarly, treatment with 10 nM EGF only weakly activated p38 and JNK1. By contrast, treatment with 40 J/m$^2$ UV-C, 300 mM sorbitol, 10 ng/ml interleukin-1, and 10 ng/ml TNFA strongly activated p38 and JNK1 activity. The effect of LPS on the activity of p38 was examined using CHO cells that express human CD14. Exposure of CHO cells to 10 ng/ml LPS only slightly activated p38 and JNK1 activity.

TABLE 2 p38 AND JNK1 ACTIVATION BY PRO-INFLAMMATORY CYTOKINES AND ENVIRONMENTAL STRESS.

| | Relative Protein Kinase Activity | |
|---|---|---|
| | JNK | p38 |
| Control | 1.0 | 1.0 |
| Epidermal Growth Factor (10 nM) | 1.9 | 2.1 |
| Phorbol Ester (10 nM) | 2.3 | 2.9 |
| Lipopolysaccharide (10 ng/ml) | 3.6 | 3.7 |
| Osmotic Shock (300 mM sorbitol) | 18.1 | 4.2 |
| Tumor Necrosis Factor (10 ng/ml) | 19.3 | 10.3 |
| Interleukin-1 (10 ng/ml) | 8.9 | 6.2 |
| UV (40 J/m$^2$) | 7.4 | 17.1 |

EXAMPLE 18 p38 MAP Kinase Activation by Dual Phosphorylation on Tyr and Thr

COS-1 cells expressing wild-type (Thr1$^{180}$, Tyr$^{182}$) or mutated (Ala$^{180}$, Phe $^{182}$) p38 MAP kinase were treated without and with UV-C (40 J/m$^2$). The cells were harvested 30 minutes following exposure with or without UV radiation. Control experiments were performed using mock-transfected cells. The level of expression of epitope-tagged p38 MAP kinase and the state of Tyr phosphorylation of p38 MAP kinase was examined by Western blot analysis using the M2 monoclonal antibody and the phosphotyrosine monoclonal antibody PY20. Immune complexes were detected by enhanced chemiluminescence.

Wild-type and mutant p38 were expressed at similar levels. Western blot analysis showed that UV radiation caused an increase in the Tyr phosphorylation of p38. The increased Tyr phosphorylation was confirmed by phospho-amino acid analysis of p38 isolated from [$^{32}$P] phosphate-labeled cells. The results also showed that UV radiation increased Thr phosphorylation of p38. The increased phosphorylation on Tyr and Thr was blocked by mutated p38. Wild-type and mutated p38 were isolated from the COS-1 cells by immunoprecipitation. Protein kinase activity was measured in the immune complex using [γ-$^{32}$P]ATP and GST-ATF2 as substrates. The phosphorylated GST-ATF2 was detected after SDS-PAGE by autoradiography. UV radiation resulted in a marked increase in the activity of wild-type p38, while the mutant p38 was found to be catalytically inactive. These results show that p38 is activated by dual phosphorylation within the Thr-Gly-Tyr motif.

EXAMPLE 19

MAP Kinase Phosphatase Inhibits p38 MAP kinase Activation

The cells were treated without and with 40 J/m$^2$ UV-C. Control experiments were performed using mock-transfected cells (control) and cells transfected with the catalytically inactive mutated phosphatase mPAC1 (Cys$^{257}$/Ser) and human MKP1. The activity of p38 MAP kinase was measured with an immunecomplex protein kinase assay employing [γ-$^{32}$P ]ATP and GST-ATF2 as substrates. The expression of PAC1 or MKP1 was found to inhibit p38 phosphorylation, demonstrating that p38 can be regulated by the dual specificity phosphatases PAC1 and MKP1.

EXAMPLE 20

Subcellular Distribution of p38 MAP Kinase

Epitope-tagged p38 MAP kinase was expressed in COS cells. The cells were treated without or with 40 J/m$^2$ UV radiation and then incubated for 60 minutes at 37° C. The p38 MAP kinase was detected by indirect immunofluorescence using the M2 monoclonal antibody. The images were acquired by digital imaging microscopy and processed for image restoration.

Immunocytochemistry. Coverslips (22 mm×22 mm No. 1; Gold Seal Cover Glass; Becton-Dickinson) were pre-treated by boiling in 0.1 N HCl for 10 minutes, rinsed in distilled water, autoclaved and coated with 0.01% poly-L-lysine (Sigma; St. Louis Mo.). The coverslips were placed at the bottom of 35 mm multiwell tissue culture plates (Becton Dickinson, UK). Transfected COS-1 cells were plated directly on the coverslips and allowed to adhere overnight in Dulbecco's modified Eagle's medium supplemented with 5% fetal calf serum (Gibco-BRL). 24 hours post-transfection, the cells were rinsed once and incubated at 37° C. for 30 minutes in 25 mM Hepes, pH 7.4, 137 mM NaCl, 6 mM KCl, 1 mM MgCl$_2$, 1 mM CaCl$_2$, 10 mM glucose. The cells were rinsed once with phosphate-buffered saline and the coverslips removed from the tissue culture wells. Cells were fixed in fresh 4% paraformaldehyde in phosphate-buffered saline for 15 minutes at 22° C. The cells were permeabilized with 0.25% TRINTON®X-100 in phosphate-buffered saline for 5 minutes and washed three times in DWB solution (150 mM NaCl, 15 mM Na citrate, pH 7.0, 2% horse serum, 1% (w/v) bovine serum albumin, 0.05% TRINTON®X-100) for 5 minutes. The primary antibody (M2 anti-FLAG monoclonal antibody, Eastman-Kodak Co., New Haven, Conn.) was diluted 1:250 in DWB and applied to the cells in a humidified environment at 22° C. for 1 hour. The cells were again washed three times as above and fluorescein isothiocyanate-conjugated goat anti-mouse Ig secondary antibody (Kirkegaard & Perry Laboratories Inc. Gaithersburg, Md.) was applied at a 1:250 dilution for 1 hour at 22° C. in a humidified environment. The cells were then washed three times in DWB and then mounted onto slides with Gel-Mount (Biomeda Corp. Foster City, Calif.) for immunofluorescence analysis. Control experiments were performed to assess the specificity of the observed immunofluorescence. No fluorescence was detected when the transfected cells were stained in the absence of the primary M2 monoclonal antibody, or mock-transfected cells.

Digital Imaging Microscopy and Image Restoration

Digital images of the fluorescence distribution in single cells were obtained using a Nikon 60x Planapo objective (numerical aperture=1.4) on a Zeiss IM-35 microscope equipped for epifluorescence as previously described (Carrington et al. (1990) in: Non-invasive Techniques in Cell Biology (Fosbett & Grinstein, eds.), Wiley-Liss, NY; pp. 53–72; Fay et al. (1989) J. Microsci. 153:133–149). Images of various focal planes were obtained with a computer controlled focus mechanism and a thermoelectrically cooled charged-coupled device camera (model 220; Photometrics Ltd., Tucson, Ariz.). The exposure of the sample to the excitation source was determined by a computer-controlled shutter and wavelength selector system (MVI, Avon, Mass.). The charge-coupled device camera and microscope functions were controlled by a microcomputer, and the data acquired from the camera were transferred to a Silicon Graphics model 4D/GTX workstation (Mountainview, Calif.) for image processing. Images were corrected for non-uniformities in sensitivity and for the dark current of the charge coupled device detector. The calibration of the microscopy blurring was determined by measuring the instrument's point spread function as a series of optical sections at 0.125$\mu$m intervals of a 0.3 $\mu$m diameter fluorescently labeled latex bead (Molecular Probes Inc.). The image restoration algorithm used is based upon the theory of ill-posed problems and obtains quantitative dye density values within the cell that are substantially more accurate than those in an un-processed image (Carrington et al. (1990) supra; Fay et al. (1989) supra). After image processing, individual optical sections of cells were inspected and analyzed using computer graphics software on a Silicon Graphics workstation. p38 MAP kinase was observed at the cell surface, in the cytoplasm, and in the nucleus. After irradiation, an increased localization of cytoplasmic p38 to the perinuclear region was detected.

EXAMPLE 21

Activation of the MKK Signal Transduction Pathway by Osmotic Shock

CHO cells were co-transfected with the plasmid pCMV-Flag-Jnk1 and pRSV-Neo (Dérijard et al. (1994) supra). A stable cell line expressing epitope-tagged Jnk1 (Flag; Immunex Corp.) was isolated by selection with Geneticin (Gibco-BRL). The cells were incubated with 0, 100, 150, 300, 600, or 1000 mM sorbitol for 1 hour at 37° C. The cells were collected in lysis buffer (20 mM Tris, pH 7.4, 1% TRINTON®X-100, 2 mM EDTA, 137 mM NaCl, 25 mM β-glycerophosphate, 1 mM orthovanadate, 2 mM pyrophosphate, 10% glycerol, 1 mM phenylmethylsulfonyl fluoride, 10 $\mu$g/ml leupeptin) and a soluble extract was obtained by centrifugation at 100,000 g for 30 minutes at 4° C. The epitope-tagged JNK1 was isolated by immunoprecipitation with the monoclonal antibody M2 (Immunex Corp.). The immunoprecipitates were washed extensively with lysis buffer. Immunecomplex kinase assays were done in 25 $\mu$l of 25 mM Hepes, pH 7.4, 25 mM MgCl$_2$, 25 mM β-glycerophosphate, 2 mM dithiothreitol, 100 $\mu$M orthovanadate, and 50 $\mu$M ATP [$\gamma$-$^{32}$P] (10 Ci/mmole) with 2.5 $\mu$g of bacterially expressed c-Jun (residues 1-79) fused to glutathione-S-transferase (GST) as a substrate. The phosphorylation of c-Jun was examined after SDS-PAGE by autoradiography and PhosphorImager (Molecular Dynamics Inc.) analysis. JNK1 activation was observed at all concentrations of sorbitol exposure.

The time course of JNK1 protein kinase activation was measured in cells incubated in medium supplemented with 300 mM sorbitol as described above. Increased JNK1 activity was observed within 5 minutes of exposure to sorbitol, with maximum activity occurring after 15–30 minutes.

Mutation of JNK1 at the phosphorylation sites Thr$^{183}$ and Tyr$^{185}$ blocked the activation of JNK1 protein kinase activity by osmotic shock. CHO cells were transfected with vector, wild-type JNK1 (Thr$^{183}$, Tyr$^{185}$), and mutated JNK1 (Ala$^{183}$, Phe$^{185}$). The cells were incubated in medium supplemented without or with 300 mM sorbitol for 15 minutes before measurement of JNK1 protein kinase activity as described above. JNK1 activation was seen in the wild-type but not mutated JNK1.

Use

The MKK polypeptides and polynucleotides of the invention are useful for identifying reagents which modulate the MKK signal transduction pathways. Reagents that modulate an MKK signal transduction pathway can be identified by their effect on MKK synthesis, MKK phosphorylation, or MKK activity. For example, the effect of a reagent on MKK activity can be measured by the in vitro kinase assays described above. MKK is incubated without (control) and with a test reagent under conditions sufficient to allow the components to react, then the effect of the test reagent on kinase activity is subsequently measured. Reagents that inhibit an MKK signal transduction pathway can be used in the treatment of MKK-mediated disorders. Reagents that stimulate an MKK signal transduction pathway can be used in a number of ways, including induction of programmed cell death (apoptosis) in tissues. For example, the elimination of UV damaged cells can be used to prevent cancer.

Generally, for identification of a reagent that inhibits the MKK signal transduction pathway, the kinase assay is tested with a range of reagent concentrations, e.g., 1.0 nM to 100 mM, a MKK substrate, and a radioactive marker such as $[\gamma^{-32}P]$ATP. Appropriate substrate molecules include p38, JNK1, JNK2, or ATF2. The incorporation of $[^{32}P]$ into the substrate is determined, and the results obtained with the test reagent compared to control values. Of particular interest are reagents that result in inhibition of $[^{32}P]$ of about 80% or more.

Assays that test the effect of a reagent on MKK synthesis can also be used to identify compounds that inhibit MKK signal transduction pathways. The effect of the test reagent on MKK expression is measured by, for example, Western blot analysis with an antibody specific for MKK. Antibody binding is visualized by autoradiography or chemiluminescence, and is quantitated. The effect of the test reagent on MKK mRNA expression can be examined, for example, by Northern blot analysis using a polynucleotide probe or by polymerase chain reaction.

Reagents found to inhibit MKK signal transduction pathways can be used as therapeutic agents for the treatment of MKK-mediated disorders. Such reagents are also useful in drug design for elucidation of the specific molecular features needed to inhibit MKK signal transduction pathways.

In addition, the invention provides a method for the treatment of MKK-mediated stress-related and inflammatory disorders. The method includes administration of an effective amount of a therapeutic reagent that inhibits MKK function. Suitable reagents inhibit either MKK activity or expression. The concentration of the reagent to be administered is determined based on a number of factors, including the appropriate dosage, the route of administration, and the specific condition being treated. The appropriate dose of a reagent is determined by methods known to those skilled in the art including routine experimentation to optimize the dosage as necessary for the individual patient and specific MKK-mediated disorder being treated. Specific therapeutically effective amounts appropriate for administration are readily determined by one of ordinary skill in the art (see, for example, *Remington's Pharmaceutical Sciences*. 18th ed., Gennaro, ed., Mack Publishing Company, Easton, Pa., 1990).

The invention provides methods for both acute and prophylactic treatment of stress-related and inflammatory disorders. For example, it is envisioned that ischemic heart disease will be treated during episodes of ischemia and oxidative stress following reperfusion. In addition, a patient at risk for ischemia can be treated prior to ischemic episodes.

In another example, a therapeutic agent which inhibits MKK function or activity is administered to control inflammatory responses by inhibiting the secretion of inflammatory cytokines, including TNF and IL-1.

Stress-related proliferative disorders can also be treated by the method of the invention by administering a therapeutic reagent that inhibits MKK function or activity. Such therapeutic reagents can be used alone or in combination with other therapeutic reagents, for example, with chemotherapeutic agents in the treatment of malignancies. Indeed, the control of stress-activated MKK by the therapeutic reagents provided by this invention can modulate symptoms caused by other therapeutic strategies that induce stress.

The therapeutic reagents employed are compounds which inhibit MKK function or activity, including polynucleotides, polypeptides, and other molecules such as antisense oligonucleotides and ribozymes, which can be made according to the invention and techniques known to the art. Polyclonal or monoclonal antibodies (including fragments or derivatives thereof) that bind epitopes of MKK also can be employed as therapeutic reagents. Dominant-negative forms of MKK which effectively displace or compete with MKK for substrate binding and/or phosphorylation can be used to decrease protein kinase activity. Dominant-negative forms can be created by mutations within the catalytic domain of the protein kinases, as described above.

In some cases, augmentation of MKK activity is desirable, e.g., induction of apoptosis. The methods of the invention can be used to identify reagents capable of increasing MKK function or activity. Alternatively, increased activity is achieved by over-expression of MKK. When a MKK-mediated disorder is associated with under-expression of MKK, or expression of a mutant MKK polypeptide, a sense polynucleotide sequence (the DNA coding strand) or MKK polypeptide can be introduced into the cell.

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a polypeptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and the like. Preservatives and other additives can also be present, such as, for example, antimicrobials, antioxidants, chelating agents, and inert gases, and the like.

Polynucleotide sequences, including antisense sequences, can be therapeutically administered by various techniques known to those skilled in the art. Such therapy would achieve its therapeutic effect by introduction of the MKK polynucleotide into cells of mammals having a MKK-mediated disorder. Delivery of MKK polynucleotides can be achieved using free polynucleotide or a recombinant expression vector such as a chimeric virus or a colloidal dispersion system. Especially preferred for therapeutic delivery of nucleotide sequences is the use of targeted liposomes.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

We claim:

1. A substantially pure human mitogen-activated protein kinase kinase (MKK) polypeptide having serine, threonine, and tyrosine kinase activity, wherein said MKK polypeptide phosphorylates human mitogen-activated protein (MAP) kinase p38, has a molecular weight of about 36 kD, and is encoded by a nucleic acid sequence that hybridizes under stringent conditions to a sequence fully complementary to the nucleic acid sequence of GenBank accession number L36719.

2. A polypeptide of claim 1 comprising the amino acid sequence of SEQ ID NO:2.

3. A substantially pure human mitogen-activated protein kinase kinase (MKK) polypeptide having serine, threonine, and tyrosine kinase activity, wherein said MKK polypeptide phosphorylates human mitogen-activated protein (MAP) kinase p38 and human c-Jun amino-terminal kinase (JNK), has a molecular weight of about 44 kD, and is encoded by a nucleic acid sequence that hybridizes under stringent conditions to a sequence fully complementary to the nucleic acid sequence of GenBank accession number L36870.

4. A polypeptide of claim 3 comprising the amino acid sequence of SEQ ID NO:1.

\* \* \* \* \*